(12) United States Patent
Short

(10) Patent No.: US 6,846,627 B2
(45) Date of Patent: Jan. 25, 2005

(54) SCREENING FOR NOVEL COMPOUNDS WHICH REGULATE BIOLOGICAL INTERACTIONS

(75) Inventor: Jay M. Short, Rancho Santa Fe, CA (US)

(73) Assignee: Diversa Corporation, San Diego, CA (US)

( * ) Notice: Subject to any disclaimer, the term of this patent is extended or adjusted under 35 U.S.C. 154(b) by 141 days.

(21) Appl. No.: 09/529,458

(22) PCT Filed: Oct. 15, 1998

(86) PCT No.: PCT/US98/21895

§ 371 (c)(1),
(2), (4) Date: May 23, 2000

(87) PCT Pub. No.: WO99/19518

PCT Pub. Date: Apr. 22, 1999

(65) Prior Publication Data

US 2002/0028448 A1 Mar. 7, 2002

Related U.S. Application Data

(60) Provisional application No. 60/062,073, filed on Oct. 15, 1997.

(51) Int. Cl.[7] ................................................. C12Q 1/68
(52) U.S. Cl. ............................................. 435/6; 435/29
(58) Field of Search ............................... 435/6, 29, 7.1

(56) References Cited

U.S. PATENT DOCUMENTS

| | | | | |
|---|---|---|---|---|
| 5,322,801 A | * | 6/1994 | Kingston et al. | |
| 5,525,490 A | * | 6/1996 | Erickson et al. | |
| 5,569,588 A | | 10/1996 | Ashby et al. | |
| 5,582,995 A | | 12/1996 | Avruch et al. | ................ 435/7.1 |

FOREIGN PATENT DOCUMENTS

| | | | |
|---|---|---|---|
| WO | WO 94/09133 | 4/1994 | |
| WO | WO 95/28497 | 10/1995 | |
| WO | WO 95/34646 | 12/1995 | |
| WO | WO 97/04077 | * 2/1997 | |

OTHER PUBLICATIONS

Patanjuli et al (1991) Proc. Natl. Acad. Sci. 88:1943–1947.*
Mendelsohn et al (1995) Curr. Op. in Biotech. 5:482–486.*
Horikoshi (1995) Curr. Op. in Biotech. 6:292–297.*
Stein et al (1996) J. Bact. 178:591–599.*

Chaudhuri et al., "The interaction between the catalytic A subunit of calcineurin and its autoinhibitory domain, in the yeast two–hybrid system, is disrupted by cyclosporin A and FK506," *Federation of European Biochemical Societies* 357:221–226 (1995).

Chiu et al., "RAPT1, a mammalian homolog of yeast Tor, interacts with the FKBP12/rapamycin complex," *Proc. Natl. Acad. Sci. USA* 91:12574–12578 (Dec. 1994).

Mendelsohn and Brent, "Applications of interaction traps/two–hybrid systems to biotechnology research," *Current Opinion in Biotechnology* 5:482–486 (1994).

Vidal et al., "Reverse two–hybrid and one–hybrid systems to detect dissociation of protei—protein and DNA–protein and interactions," *Proc. Natl. Acad. Sci. USA* 93:10315–10320 (Sep. 1996).

Yang et al., "Cyclophilin A and FKBP12 Interact with YY12 and Alter Its Transcriptional Activity," *The Journal of BiologicalChemistry* 270(28):15187–15193 (Jun. 1996).

* cited by examiner

*Primary Examiner*—James Ketter
(74) *Attorney, Agent, or Firm*—Gary Cary Ware & Freidenrich, LLP

(57) ABSTRACT

Disclosed is a process for identifying compounds having a specified activity of interest, which process comprises (i) introducing interacting molecules into a host cell under conditions to generate or repress a detectable signal; and (ii) introducing a third compound or gene or genes encoding a third compound into the host cell from (i); and (iii) screening said host cell utilizing a method for detecting the inhibition or enhancement of interaction of proteins or other molecules in an in vivo or in vitro system. Another aspect of the present invention provides a process for identifying compounds of interest, which process comprises (i) generating one or more expression libraries derived from nucleic acid directly isolated from the environment; and (ii) screening said libraries utilizing a method for detecting the inhibition or enhancement of interaction of proteins or other molecules in an in vivo or in vitro system.

15 Claims, 6 Drawing Sheets

SCREENING FOR NOVEL COMPOUNDS WHICH REGULATE BIOLOGICAL INTERACTIONS

This application is a 371 of PCT Application No. PCT/US98/21895. which was tiled Oct. 15, 1998: which claims priority under 35 use 119(e) to U.S. Provisional Application No. 60/062,073 filed Oct. 15, 1997.

FIELD OF THE INVENTION

The present invention relates to a method for the discovery of new bio-active molecules, such as antibiotics, antivirals, anti-tumor agents and regulatory proteins. More particularly, the invention relates to a method for screening for the ability of these molecules to affect the interactions of other proteins or of other molecules utilizing a method for detecting the interaction of proteins or other molecules in in-vivo or in-vitro systems. The invention further relates to a system for capturing genes potentially encoding novel biochemical pathways of interest in prokaryotic or eukaryotic systems, and screening these pathways for compounds of interest utilizing the methods presented herein.

BACKGROUND OF THE INVENTION

Within the last decade there has been a dramatic increase in the need for bioactive compounds with novel activities. This demand has arisen largely from changes in worldwide demographics coupled with the clear and increasing trend in the number of pathogenic organisms that are resistant to currently available antibiotics. For example. while there has been a surge in demand for antibacterial drugs in emerging nations with young populations, countries with aging populations, such as the US. require a growing repertoire of drugs against cancer, diabetes, arthritis and other debilitating conditions. The death rate from infectious diseases has increased 58% between 1980 and 1992 and it has been estimated that the emergence of antibiotic resistant microbes has added in excess of $30 billion annually to the cost of health care in the US alone. As a response to this trend, pharmaceutical companies have significantly increased their screening of microbial diversity for compounds with unique activities or speciflcities.

There are several common sources of lead compounds (drug candidates), including natural product collections, synthetic chemical collections, and synthetic combinatorial chemical libraries, such as nucleotides, peptides, or other polymeric molecules. Each of these sources has advantages and disadvantages. The success of programs to screen these candidates depends largely on the number of compounds entering the programs, and pharmaceutical companies have to date screened hundred of thousands of synthetic and natural compounds in search of lead compounds. Unfortunately, the ratio of novel compounds to previously-discovered compounds has diminished with time. The discovery rate of novel lead compounds has not kept pace with demand despite the best efforts of pharmaceutical companies. There exists a strong need for accessing new sources of potential drug candidates.

The majority of bioactive compounds currently in use are derived from soil microorganisms. Many microbes inhabiting soils and other complex ecological communities produce a variety of compounds that increase their ability to survive and proliferate. These compounds are generally thought to be nonessential for growth of the organism and are synthesized with the aid of genes involved in intermediary metabolism hence their name—secondary metabolites. Secondary metabolites that influence the growth or survival of other organisms are known as bioactive compounds and serve as key components of the chemical defense arsenal of both micro- and macroorganisms. Humans have exploited these compounds for use as antibiotics, antiinfectives and other bioactive compounds with activity against a broad range of prokaryotic and eukuryotic pathogens. Approximately 6,000 bioactive compounds of microbial origin have been characterized, with more than 60% produced by the gram positive soil bacteria of the genus *Streptomyces*. Of these, a least 70 are currently used for biomedical and agricultural applications. The largest class of bioactive compounds, the polyketides, include a broad range of antibiotics, immunosuppressants and anticancer agents which together account for sales of over $5 billion per year.

Despite the seemingly large number of available bioactive compounds, it is clear that one of the greatest challenges facing modern biomedical science is the proliferation of antibiotic resistant pathogens. Because of their short generation time and ability to readily exchange genetic information, pathogenic microbes have rapidly evolved and disseminated resistance mechanisms against virtually all classes of antibiotic compounds. For example, there are virulent strains of the human pathogens *Staphylococcus* and *Streptococcus* that can now be treated with but a single antibiotic, vancomycin, and resistance to this compound will require only the transfer of a single gene, vanA, from resistant *Enterococcus* species for this to occur. When this crucial need for novel antibacterial compounds is superimposed on the growing demand for enzyme inhibitors, immunosuppressants and anti-cancer agents, it becomes readily apparent why pharmaceutical companies have stepped up their screening of microbial diversity for bioactive compounds with novel properties.

The approach currently used to screen microbes for new bioactive compounds has been largely unchanged since the inception of the field. New isolates of bacteria, particularly gram positive strains from soil environments, are collected and their metabolites tested for pharmacological activity. A more recent approach has been to use recombinant techniques to synthesize hybrid antibiotic pathways by combining gene subunits from previously characterized pathways. This approach, called combinatorial biosynthesis has focused primarily on the polyketide antibiotics and has resulted in a number of structurally unique compounds which have displayed activity. However, compounds with novel antibiotic activities have not yet been reported, an observation that may be due to the fact that the pathway subunits arc derived from those genes encoding previously characterized compounds. Dramatic success in using recombinant approaches to small molecule synthesis has been recently reported in the engineering of biosynthetic pathways to increase the production of desirable antibiotics.

There is still tremendous biodiversity that remains untapped as the source of lead compounds. However, the currently available methods for screening and producing lead compounds cannot be applied efficiently to these under-explored resources. For instance, it is estimated that at least 99% of marine bacteria species do not survive on laboratory media, and commercially available fermentation equipment is not optimal for use in the conditions under which these species will grow, hence these organisms are difficult or impossible to culture for screening or re-supply. Recollection, growth, strain improvement, media improvement and scale-up production of the drug-producing organisms often pose problems for synthesis and development of lead compounds. Furthermore, the need for the interaction of specific organisms to synthesize some compounds makes their use in discovery extremely difficult. New methods to harness the genetic resources and chemical diversity of these untapped sources of compounds for use in drug discovery are very valuable. The present invention provides a path to access this untapped biodiversity and to rapidly screen for activities of interest utilizing recombinant DNA technology. This invention combines the benefits associated with the ability to rapidly screen nature with the flexibility and reproducibility afforded with working with the genetic material of organisms.

The present invention allows one to identify genes encoding bioactivities of interest from complex environmental gene expression libraries, and to manipulate cloned pathways to evolve recombinant small molecules with unique activities. Bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. The gene cluster, the promoter, and additional sequences that function in regulation altogether are referred to as an "operon" and can include up to 20 or more genes, usually from 2 to 6 genes. Thus, a gene cluster is a group of adjacent genes that are either identical or related, usually as to their function. Gene clusters are of interest in drug discovery processes since product(s) of gene clusters include, for example, antibiotics, antivirals, antitumor agents and regulatory proteins.

Some gene families consist of one or more identical members. Clustering is a prerequisite for maintaining identity between genes, although clustered genes are not necessarily identical. Gene clusters range from extremes where a duplication is generated of adjacent related genes to cases where hundreds of identical genes lie in a tandem array. Sometimes no significance is discernable in a repetition of a particular gene. A principal example of this is the expressed duplicate insulin genes in some species, whereas a single insulin gene is adequate in other mammalian species.

Gene clusters undergo continual reorganization and thus, the ability to create heterogeneous libraries of gene clusters from, for example, bacterial or other prokaryotic sources is valuable in determining sources of novel bioactivities, including enzymes such as, for example, the polyketide synthases that are responsible for the synthesis of polyketides having a vast array of useful activities.

Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases (PKSs) are multifunctional enzymes that catalyze the biosynthesis of a wide variety of carbon chains differing in length and patterns of functionality and cyclization. Despite their apparent structural diversity, they are synthesized by a common pathway in which units derived from acetate or propionate are condensed onto the growing chain in a process resembling fatty acid biosynthesis. The intermediates remain bound to the polyketide synthase during multiple cycles of chain extension and (to a variable extent) reduction of the -ketone group formed in each condensation. The structural variation between naturally occurring polyketides arises largely from the way in which each PKS controls the number and type of units added, and from the extent and stereochemistry of reduction at each cycle. Still greater diversity is produced by the action of regiospecific glycosylases, methyltransferases and oxidative enzymes on the product of the PKS.

Polyketide synthase genes fall into gene clusters. At least one type (designated type I) of polyketide synthases have large size genes and encoded enzymes, complicating genetic manipulation and in vitro studies of these genes/proteins. Progress in understanding the enzymology of such type I systems has previously been frustrated by the lack of cell-free systems to study polyketide chain synthesis by any of these multienzymes, although several partial reactions of certain pathways have been successfully assayed in vitro. Cell-free enzymatic synthesis of complex polyketides has proved unsuccessful, despite more than 30 years of intense efforts, presumably because of the difficulties in isolating fully active forms of these large, poorly expressed multifunctional proteins from naturally occurring producer organisms, and because of the relative lability of intermediates formed during the course of polyketide biosynthesis. In an attempt to overcome some of these limitations, modular PKS subunits have been expressed in heterologous hosts such as *Escherichia coli* and *Streptomyces coelicolor*. Whereas the proteins expressed in *E. coli* are not fully active, heterologous expression of certain PKSs in *S.coelicolor* resulted in the production of active protein. Cell-free enzymatic synthesis of polyketides from PKSs with substantially fewer active sites, such as the 6-methylsalicylate synthase, chalcone synthase, tetracenomycin synthase, and the PKS responsible for the polyketide component of cyclosporin, have been reported.

Hence, studies have indicated that in vitro synthesis of polyketides is possible, however, synthesis was always performed with purified enzymes. Heterologous expression of genes encoding PKS modular subunits have allowed synthesis of functional polyketides in vivo, however, there are several challenges presented by this approach, which had to be overcome. The large size of modular PKS gene clusters (>30 kb) make their manipulation on plasmids difficult. Modular PKSs also often utilize substrates which may be absent in a heterologous host. Finally, proper folding, assembly, and posttranslational modification of very large foreign polypeptides are not guaranteed.

The present invention further relates to a method for discovering molecules which affect the interaction of proteins or other molecules in in vivo or in vitro systems through the use of fused genes encoding hybrid proteins or fused molecules capable of generating or inhibiting, or causing the generation of or inhibition of, a detectable signal.

The analysis of interactions between proteins and/or other molecules is a fundamental area of inquiry in biology. For instance, ligand:receptor interactions and the receptor/effector coupling mediated by Guanine nucleotide-binding proteins (G-proteins) are of interest in the study of disease. A large number of G protein-linked receptors funnel extracellular signals as diverse as hormones, growth factors, neurotransmitters, primary sensory stimuli, and other signals through a set of G proteins to a small number of second-messenger systems. The G proteins act as molecular switches with an "on" and "off" state governed by a GTPase cycle. Mutations in G proteins may result in either constitutive activation or loss of expression mutations. Given the variety of functions subserved by G protein-coupled signal transduction, it is not surprising that abnormalities in G protein-coupled pathways can lead to diseases with manifestations as dissimilar as blindness, hormone resistance, precocious puberty and neoplasia. G-protein-coupled receptors are extremely important to drug research efforts. It is estimated that up to 60% of today's prescription drugs work by somehow interacting with G protein-coupled receptors. However, these drugs were developed using classical medicinal chemistry and without a knowledge of the molecular mechanism of action. A more efficient drug discovery program could be deployed by targeting individual receptors and making use of information on gene sequence and biological function to develop effective therapeutics. The present invention allows one to, for example, study molecules which affect the interaction of G proteins with receptors, or of ligands with receptors.

Proteins are complex macromolecules made up of covalently linked chains of amino acids. Each protein assumes a unique three dimensional shape determined principally by its sequence of amino acids. Many proteins consist of smaller units termed domains, which are continuous stretches of amino acids able to fold independently from the rest of the protein. Some of the important forms of proteins are enzymes, polypeptide hormones, nutrient transporters, structural components of the cell, hemoglobins, antibodies, nucleoproteins, and components of viruses.

Protein-protein interactions enable two or more proteins to associate. A large number of non-covalent bonds form between the proteins when two protein surfaces are precisely matched, and these bonds account for the specificity of recognition. Protein-protein interactions are involved, for example, in the assembly of enzyme subunits; in antigen-antibody reactions, in forming the supramolecular structures of ribosomes, filaments and viruses; in transport; and in the interaction of receptors on a cell with growth factors and hormones. Products of oncogenes can give rise to neoplastic transformation through protein-protein interactions. For example, some oncogenes encode protein kinases whose enzymatic activity on cellular target proteins leads to the cancerous state. Another example of a protein-protein interaction occurs when a virus infects a cell by recognizing a polypeptide receptor on the surface, and this interaction has been used to design antiviral agents.

Protein-protein interactions have been generally studied in the past using biochemical techniques such as cross-linking, co-immunoprecipitation and co-fractionation by chromatography. A disadvantage of these techniques is that interacting proteins often exist in very low abundance and are, therefore, difficult to detect. Another major disadvantage is that these biochemical techniques involve only the proteins, not the genes encoding them. When an interaction is detected using biochemical methods, the newly identified protein often must be painstakingly isolated and then sequenced to enable the gene encoding it to be obtained. Another disadvantage is that these methods do not immediately provide information about which domains of the interacting proteins are involved in the interaction. Another disadvantage is that small changes in the composition of the interacting proteins cannot be tested easily for their effect on the interaction.

To avoid the disadvantages inherent in the biochemical techniques for detecting protein-protein interactions, genetic systems have recently been designed. One such system is based on transcriptional activation. Transcription is the process by which RNA molecules are synthesized using a DNA template. Transcription is regulated by specific sequences in the DNA which indicate when and where RNA synthesis should begin. These sequences correspond to binding sites for proteins, designated transcription factors, which interact with the enzymatic machinery used for the RNA polymerization reaction. There is evidence that transcription can be activated through the use of two functional domains of a transcription factor: a domain that recognizes and binds to a specific site on the DNA and a domain that is necessary for activation, as reported by Keegan, et al., Science 231, 699–704 (1986) and Ma and Ptashne, Cell, 48, 847–853 (1987). The transcriptional activation domain is thought to function by contacting other proteins involved in transcription. The DNA-binding domain appears to function to position the transcriptional activation domain on the target gene which is to be transcribed. In a few cases now known, these two functions (DNA-binding and activation) reside on separate proteins. One protein binds to the DNA, and the other protein, which activates transcriptions binds to the DNA-bound protein, as reported by McKnight et al., Proc. Nat'l Acad. Sci. USA, 89, 7061–7065 (1987); another example is reviewed by Curran et al., Cell, 55, 395–397 (1988).

Transcriptional activation has been studied using the GAL4 protein of the yeast Saccharomyces cerevisiae. The GAL4 protein is a transcriptional activator required for the expression of genes encoding enzymes of galactose utilization , see Johnston, Microbiol. Rev., 51, 458–476 (1987). It consists of an N-terminal domain which binds to specific DNA sequences designated UASG, (UAS stands for upstream activation site, G indicates the galactose genes) and a C-terminal domain containing acidic regions, which is necessary to activate transcription, see Keegan et al. (1986), supra., and Ma and Ptashne (1987), supra. As discussed by Keegan et al., the N-terminal domain binds to DNA in a sequence-specific manner but fails to activate transcription. The C-terminal domain cannot activate transcription because it fails to localize to the UASG, see for example Brent and Ptashne, Cell, 43, 729–736 (1985). However Ma and Ptashne have reported (Cell, 51, 113–119 (1987); Cell, 55, 443–446 (1988)) that when both the GAL4 N-terminal domain and the C-terminal domain are fused together in the same protein, transcriptional activity is induced. Other proteins also function as transcriptional activators via the same mechanism. For example, the GCN4 protein of Saccharomyces cerevisiae as reported by Hope and Struhl, Cell, 46, 885–894 (1986), the ADR1 protein of Saccharomyces cerevisiae as reported by Thukral et al., Molecular and Cellular Biology, 9, 2360–2369, (1989) and the human estrogen receptor, as discussed by Kumar et al., Cell, 51, 941–951 (1987) both contain separable domains for DNA binding and for maximal transcriptional activation.

Genetic systems that are capable of rapidly detecting which proteins interact with a known protein, determining which domains of the proteins interact, and providing the genes for the newly identified interacting proteins have recently been made available in Saccharomyces cerevisiae (Fields, S. and Song, O. (1989) Nature 340: 245–247, Mullinax, R. L., and Sorge, J. A. (1995) Strategies 8:3–5). These systems are useful for studying protein-protein interactions in-vivo in a eukaryotic host. To date, this has been viewed as advantageous because of the conditions in eukaryotic hosts that may provide for folding, solubility and post-translational modifications (such as phosphorylation) that may not occur in prokaryotic systems. Many eukaryotic proteins synthesized in bacteria fold incorrectly or inefficiently and, consequently, exhibit low specific activities. Production of authentic, biologically active eukaryotic proteins from cloned DNA frequently requires post-translational modifications such as accurate disulfide bond formation, glycosylation, phosphorylation, oligomerization, or specific proteolytic cleavage-processes that are not performed by bacterial cells. This problem is particularly severe when expression of functional membrane or secretory proteins such as cell surface receptors and extracellular hormones or enzymes is required. Thus, the need to develop these systems in prokaryotic screening hosts was not apparent and the advantages of such a system were not evident until recently.

With the advent of the ability to access uncultivated organisms in samples and archive the genes of these samples in cloning vectors in the form of gene libraries for eventual screening for bioactive molecules, the need to utilize systems that allow for the screening of very large numbers of clones has rapidly surfaced. Effective screening of these gene libraries requires systems that provide high transformation efficiencies where one can access the millions of clones representing these samples to screen. Eukaryotic systems such as those described are unfortunately plagued with lower transformation efficiencies. The ability to work in a prokaryotic host is advantageous. Hence, a major advantage of working with prokaryotic hosts, such as bacteria, lies in the high transformation efficiencies afforded by the utilization of these hosts for screening. Furthermore, in working with the eukaryotic hosts described above, it is critical that proteins are targeted to the nucleus, since the interaction has to take place in the nucleus.

Recently, a genetic system to detect protein-protein interactions in vivo using transcriptional repression as an assay in *E.coli* has been described. Genes encoding two interacting proteins are fused to a wild type and a mutant LexA DNA binding domain (the mutant is a truncated LexA protein devoid of its own oligomerization domain and is termed LexA408). LexA is an efficient transcriptional repressor in *E.coli* only if it acts as a dimer. This property is used to exchange the LexA dimerization domain by heterologous interacting motifs to recover repression. The non-covalent interaction between the hybrid proteins is probed by their capacity to restore the repressor activity of truncated LexA proteins (LexA408).

The interaction or association of the fused proteins is specifically measured using a reporter gene controlled by a hybrid sulA operator containing a wild type half-site and a mutated half-site (op408/op+) in a reporter strain (SU202). The lacZ reporter gene is under control of the op408/op+ hybrid operator using the sula promoter, the most tightly repressed naturally occurring SOS promoter. Upon co-expression of interacting fusion proteins, lacZ is repressed. A Lac+ phenotype yields red colonies with the system, and a Lac- phenotype yields white colonies.

Protein fusions have also been used to detect and characterize protein-protein interactions in *E.coli* using the phage repressor (Hu J. C. et al., Science 250, 1400–1403 (1990)). The NH-terminal DNA-binding domain of bacteriophage repressor dimerizes inefficiently and requires a separate COOH-terminal dimerization domain to bind strongly to its operator. This property allows one to evaluate the interaction between hybrid proteins generated utilizing the binding domain and the dimerization domain by their capacity to restore the repressor activity of the repressor.

In addition to protein-protein interactions, the study of the interaction of other molecules, and the ability to affect this interaction, is of interest in research and discovery processes and in the discovery of new drugs, for instance, steroids and their receptors, or polysaccharides and their receptors.

SUMMARY OF THE INVENTION

The present invention allows one to clone genes potentially encoding novel biochemical pathways of interest in eukaryotic and/or prokaryotic systems, and screen for these pathways utilizing a novel process. Sources of the genes may be isolated, individual organisms ("isolates"), collections of organisms that have been grown in defined media ("enrichment cultures"), or, most preferably, uncultivated organisms ("environmental samples"). The use of a culture-independent approach to directly clone genes encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

In the evaluation of complex environmental expression libraries, a rate limiting step occurs at the level of discovery of bioactivities. The present invention allows the screening of complex environmental expression libraries, containing, for example, thousands of different organisms.

In the present invention, for example, gene libraries generated from one or more uncultivated microorganisms are screened for an activity of interest. Potential gene pathways encoding bioactive molecules of interest are first captured in prokaryotic cells in the form of gene expression libraries and screened for activities of interest utilizing the methods of the present invention. Screening hosts can be modified to contain proteins or other molecules from metabolically rich cell lines which can aid in the expression of bioactive compounds such as small molecules.

Thus, the present invention also allows for the transfer of cloned pathways derived from uncultivated samples into hosts for heterologous expression and downstream screening for bioactive compounds of interest using the methods described herein.

The present invention provides a method for screening of recombinant bioactive and evolved compounds in vivo or in vitro using a system which can detect enhancers and inhibitors of protein-protein or other interactions, such as those between receptors and their cognate targets. The present invention further provides a method for screening of recombinant bioactive, evolved, or other compounds which can affect the interaction of molecules which interact with membrane-bound molecules (such as G-proteins).

An object of this invention is to provide a method by which a multiplicity of proteins, such as those encoded by the entire genome of a cell, can be simultaneously tested for inhibition or enhancement of other protein-protein interactions or the interactions of other molecules. It is a further object of the present invention to provide a method for detection of inhibition or enhancement of protein-protein interactions in which the nucleic acid fragments which encode the interacting proteins and potentially the inhibitor or enhancer are immediately available when a positive test occurs.

Yet another object of the present invention is to provide a method for the identification of new genes and new gene pathways. Novel systems to clone and screen for bioactivities of interest are desirable. The method(s) of the present invention allow the cloning and discovery of novel, useful bioactive molecules, and in particular novel bioactive molecules derived from uncultivated samples. The method(s) of the present invention further allow one to screen utilizing well known genetic systems.

Accordingly, in one aspect, the present invention provides a process for identifying clones encoding a specified activity of interest, which process comprises (i) generating one or more expression libraries derived from nucleic acid directly isolated from the environment; and (ii) screening said libraries utilizing a method for detecting the inhibition or enhancement of interaction of proteins or other molecules in an in vivo or in vitro system.

Another aspect of the present invention provides a process for identifying compounds of interest, which process comprises (i) introducing interacting molecules into a host cell under conditions to generate or repress a detectable signal; and (ii) introducing a third compound or gene or genes encoding a third compound into the host cell from (i); and (iii) screening said host cell utilizing a method for detecting the inhibition or enhancement of interaction of proteins or other molecules in an in vivo or in vitro system.

DETAILED DESCRIPTION OF PREFERRED EMBODIMENTS

Figure 1:
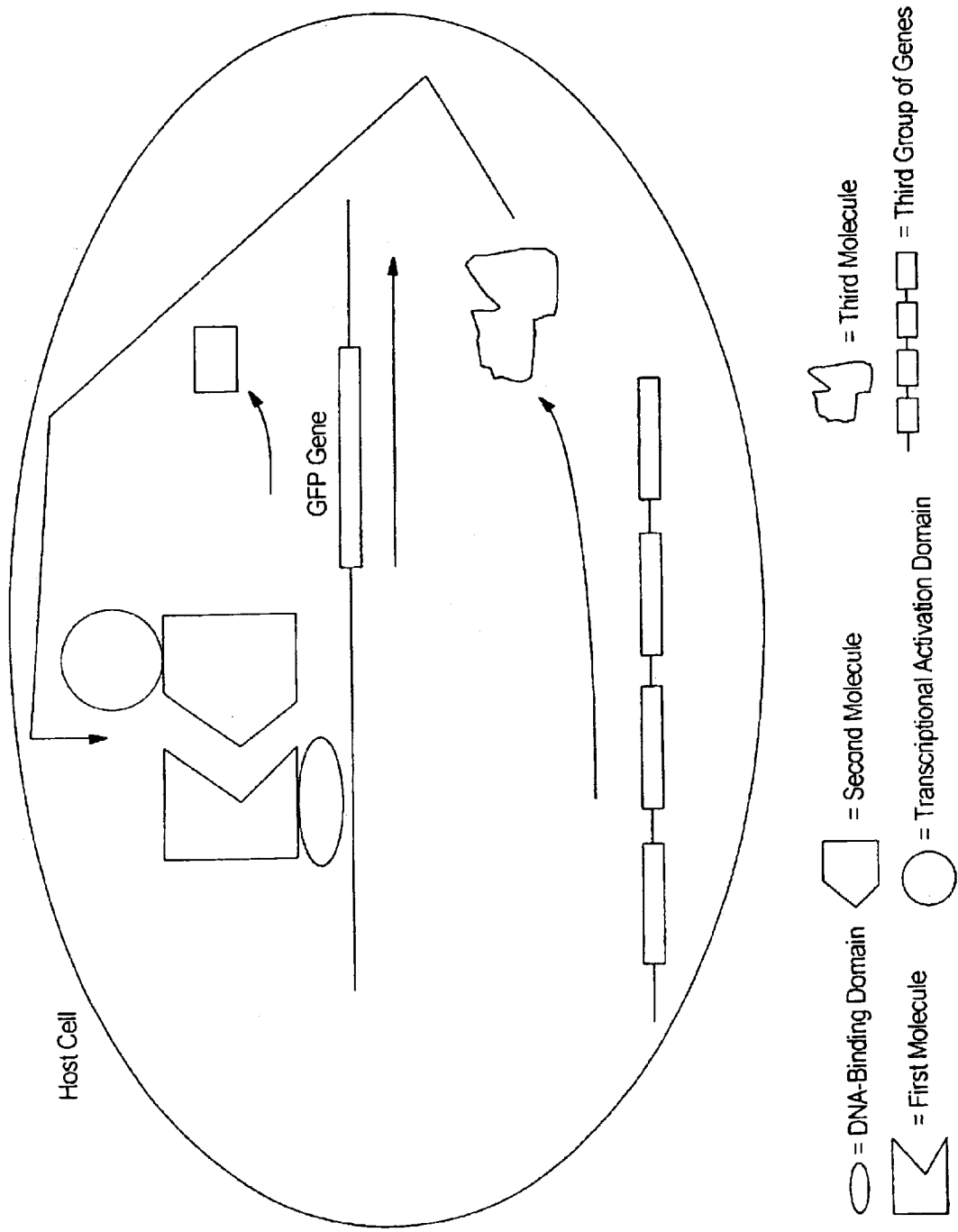
FIG. 1 shows one method of the present invention, which represents an approach to screen for small molecules that enhance or inhibit protein-protein or other interactions. The DNA binding domain and transcriptional activation domain proteins are associated with first and second interacting molecules. Interaction of the first and second molecules causes transcriptional activation of the detectable gene (GFP). A gene or group of genes encoding a third molecule is introduced into the host cell, and the ability of the third molecule to affect the interaction of the first and second molecules is evaluated. For example, clones which alter expression of the detectable gene can be sorted by FACS and the pathway clone isolated for characterization.
Figure 2:
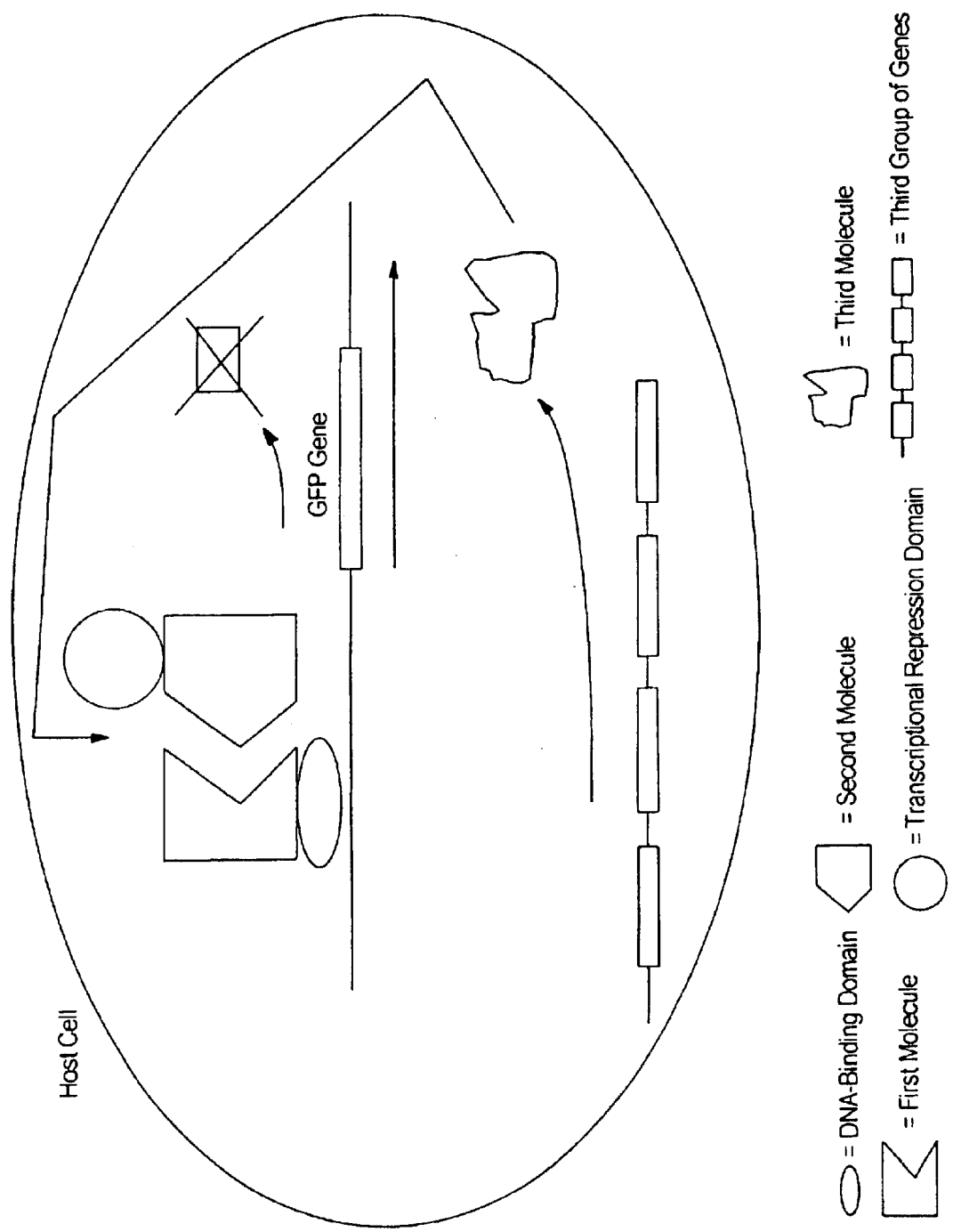
FIG. 2 shows another method of the present invention, which represents an approach to screen for small molecules that enhance or inhibit protein-protein or other interactions. The DNA binding domain and transcriptional repression domain proteins are associated with first and second interacting molecules. Interaction of the first and second molecules promotes transcriptional repression of the detectable gene (GFP). A gene or group of genes encoding a third molecule is introduced into the host cell, and the ability of the third molecule to affect the interaction of the first and second molecules is evaluated. For instance, clones which alter expression of the detectable gene can be sorted by FACS and the pathway clone isolated for characterization.
Figure 3:
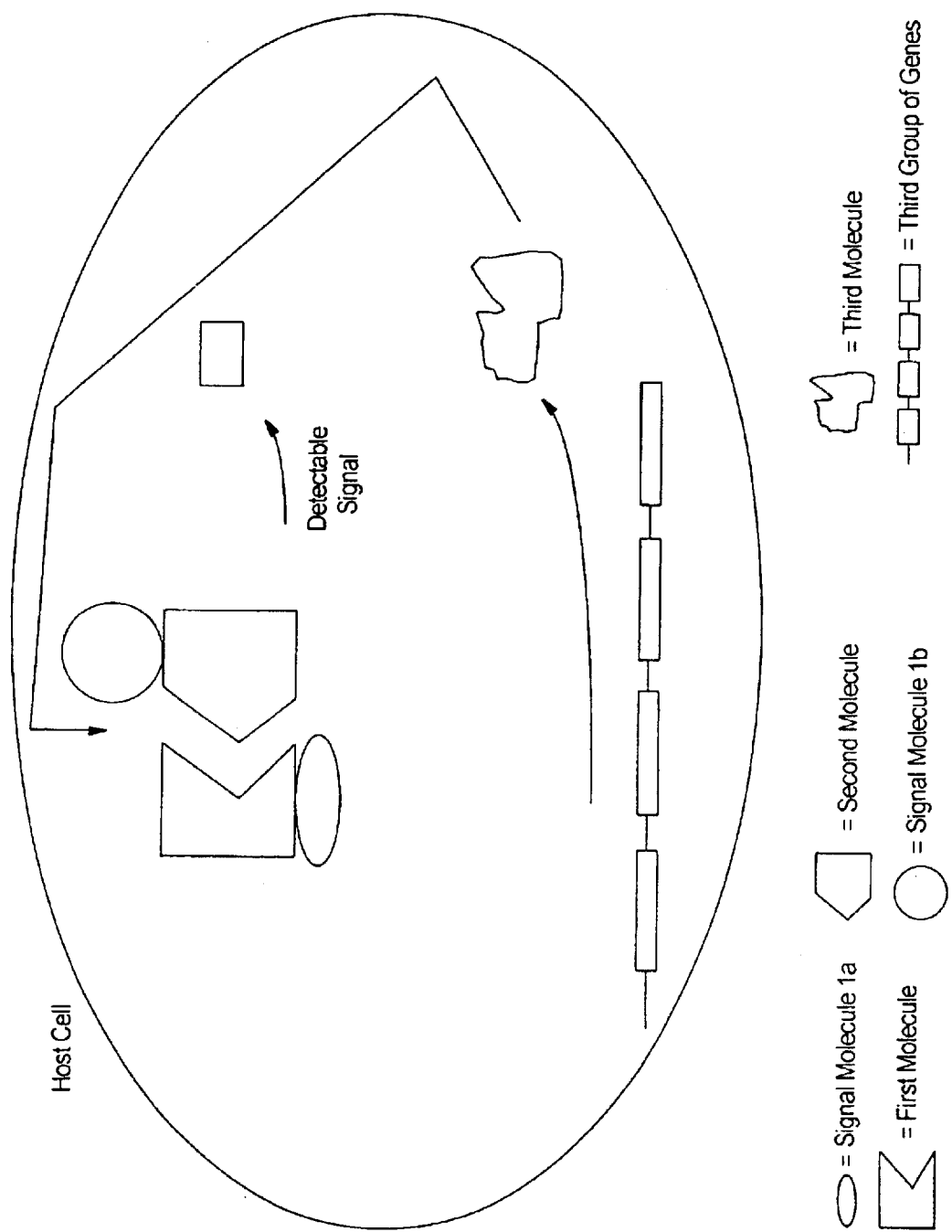
FIG. 3 shows another method of the present invention, which represents an approach to screen for molecules that enhance or inhibit protein-protein or other interactions. Signal molecules, or molecules which generate a detectable signal when they are in sufficient proximity to each other, are associated with first and second interacting molecules. Interaction of the first and second molecules generates a detectable signal. A gene or group of genes encoding a third molecule is introduced into the host cell, and the ability of the third molecule to affect the interaction of the first and second molecules is evaluated. For instance, clones which alter the presence of the detectable signal molecule can be sorted by FACS and the pathway clone isolated for characterization.
Figure 4:
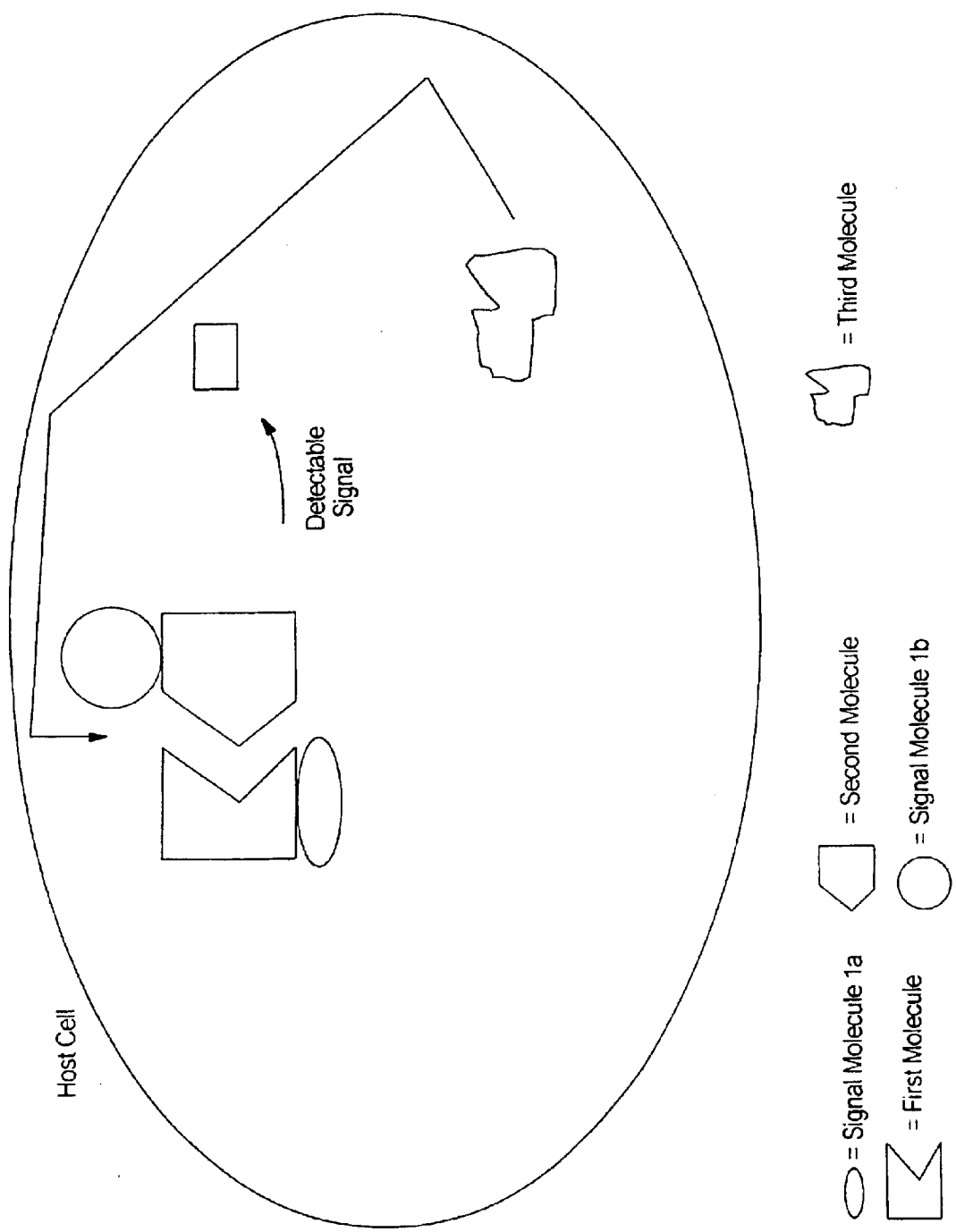
FIG. 4 shows another method of the present invention, which represents an approach to screen for molecules that enhance or inhibit protein-protein or other interactions. Signal molecules, or molecules which generate a detectable signal when they are in sufficient proximity to each other, are associated with first and second interacting molecules. Interaction of the first and second molecules generates a detectable signal. A third molecule is introduced into the host cell, and the ability of the third molecule to affect the interaction of the first and second molecules is evaluated. For instance, molecules which alter the presence of the detectable signal molecule can be sorted by FACS.
Figure 5:
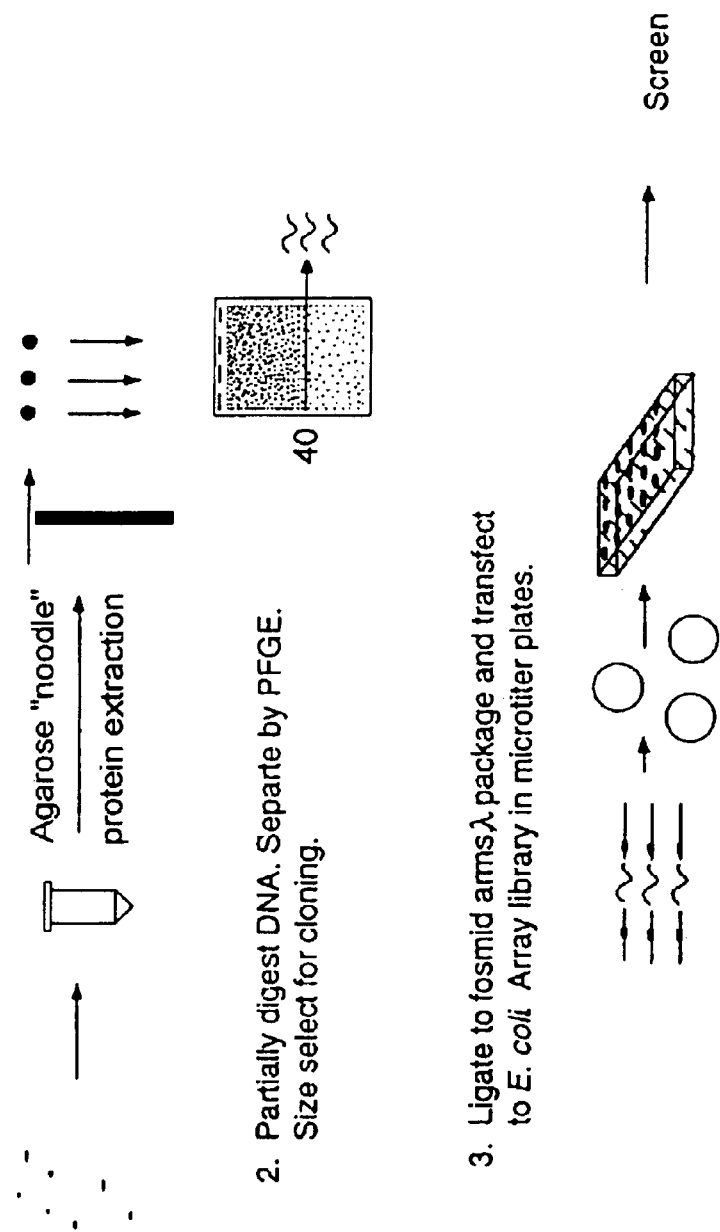
FIG. 5 shows a scheme to capture, clone and archive large genome fragments from uncultivated microbes from natural environments. Cloning vectors can be used in this process which can archive from 40 kbp (fosmids) to greater than 100 kbp (BACs).

The method of the present invention begins with the construction of gene libraries which represent the collective genomes of naturally occurring organisms archived in cloning vectors that can be propagated in suitable prokaryotic hosts.

The microorganisms from which the libraries may be prepared include prokaryotic microorganisms, such as Eubacteria and Archaea, and lower eukaryotic microorganisms such as fungi, some algae and protozoa. Libraries may be produced from environmental samples in which case DNA may be recovered without culturing of an organism or the DNA may be recovered from one or more cultured organisms. Such microorganisms may be extremophiles, such as hyperthermophiles, thermophiles, psychrophiles, psychrotrophs, halophiles, acidophiles, and the like.

The microorganisms from which the libraries may be prepared may be collected using a variety of techniques known in the art. Samples may also be collected using the methods detailed in the example provided below. Briefly, the example below provides a method of selective in situ enrichment of bacterial and archaeal species while at the same time inhibiting the proliferation of eukaryotic members of the population. In situ enrichments can to increase the likelihood of recovering rare species and previously uncultivated members of a microbial population. If one desires to obtain bacterial and archaeal species, nucleic acids from eukaryotes in an environmental sample can seriously complicate DNA library construction and decrease the number of desired bacterial species by grazing. The method described below employs selective agents, such as antifungal agents, to inhibit the growth of eukaryotic species.

In situ enrichment is achieved by using traps composed of growth substrates and nutritional amendments with the intent to lure, selectively, members of the surrounding environmental matrix. Choice of substrates (carbon sources) and nutritional amendments (ie, nitrogen, phosphorous, etc.) is dependent upon the members of the community for which one desires to enrich. Selective agents against eukaryotic members are also added to the trap. Again, the exact composition depends upon which members of the community one desires to enrich and which members of the community one desires to inhibit. Some of the enrichment media which may be useful in pulling out particular members of the community are described in the example provided herein.

Sources of microorganism DNA as a starting material library from which target DNA is obtained are particularly contemplated to include environmental samples, such as microbial samples obtained from Arctic and Antarctic ice, water or permafrost sources, materials of volcanic origin, materials from soil or plant sources in tropical areas, etc. Thus, for example, genomic DNA may be recovered from either a culturable or non-culturable organism and employed to produce an appropriate recombinant expression library for subsequent determination of a biological activity.

DNA Isolation

The preparation of DNA from the sample is an important step in the generation DNA libraries from environmental samples composed of uncultivated organisms, or for the generation of libraries from cultivated organisms. DNA can be isolated from samples using various techniques well known in the art (Nucleic Acids in the Environment Methods & Applications, J. T. Trevors, D. D. van Elsas, Springer Laboratory, 1995). Preferably, DNA obtained will be of large size and free of enzyme inhibitors or other contaminants. DNA can be isolated directly from an environmental sample (direct lysis), or cells may be harvested from the sample prior to DNA recovery (cell separation). Direct lysis procedures have several advantages over protocols based on cell separation. The direct lysis technique provides more DNA with a generally higher representation of the microbial community, however, it is sometimes smaller in size and more likely to contain enzyme inhibitors Man DNA recovered using the cell separation technique. Very useful direct lysis techniques have been described which provide DNA of high molecular weight and high purity (Barns, 1994; Holben, 1994). If inhibitors are present, there are several protocols which utilize cell isolation which can be employed (Holben, 1994). Additionally, a fractionation technique, such as the bis-benzimide separation (cesium chloride isolation) described herein, can be used to enhance the purity of the DNA.

Isolation of total genomic DNA from extreme environmental samples varies depending on the source and quantity of material. Uncontaminated, good quality (>20 kbp) DNA is required for the construction of a representative library for the present invention. A successful general DNA isolation protocol is the standard cetyl-trimethyl-ammonium-bromide (CTAB) precipitation technique. A biomass pellet is lysed and proteins digested by the nonspecific protease, proteinase K, in the presence of the detergent SDS. At elevated temperatures and high salt concentrations, CTAB forms insoluble complexes with denatured protein, polysaccharides and cell debris. Chloroform extractions are performed until the white interface containing the CTAB complexes is reduced substantially. The nucleic acids in the supernatant are precipitated with isopropanol and resuspended in TE buffer.

For cells which are recalcitrant to lysis, a combination of chemical and mechanical methods with cocktails of various cell-lysing enzymes may be employed. Isolated nucleic acid may then further be purified using small cesium gradients.

A further example of an isolation strategy is detailed in an example below. This type of isolation strategy is optimal for obtaining good quality, large size DNA fragments for cloning.

Normalization

The present invention can further optimize methods for isolation of activities of interest from a variety of sources, including consortias of microorganisms, primary enrichments, and environmental "uncultivated" samples. Libraries which have been "normalized" in their representation of the genome populations in the original samples are possible with the present invention. These libraries can then be screened utilizing the methods of the present invention, for enzyme and other bioactivities of interest.

Libraries with equivalent representation of genomes from microbes that can differ vastly in abundance in natural populations are generated and screened. This "normalization" approach reduces the redundancy of clones from abundant species and increases the representation of clones from rare species. These normalized libraries allow for greater screening efficiency resulting in the identification of cells encoding novel biological catalysts.

In one embodiment, viable or non-viable cells isolated from the environment are, prior to the isolation of nucleic acid for generation of the expression gene library, FACS sorted to separate cells from the sample based on, for instance, DNA or AT/GC content of the cells. Various dyes or stains well known in the art, for example those described in "Practical Flow Cytometry", 1995 Wiley-Liss, Inc., Howard M. Shapiro, M.D., are used to intercalate or associate with nucleic acid of cells, and cells are separated on the FACS based on relative DNA content or AT/GC DNA content in the cells. Other criteria can also be used to separate cells from the sample, as well. DNA is then isolated from the cells and used for the generation of expression gene libraries, which are then screened for activities of interest.

Alternatively, the nucleic acid is isolated directly from the environment and is, prior to generation of the gene library, sorted based on DNA or AT/IC content. DNA isolated directly from the environment, is used intact, randomly sheared or digested to general fragmented DNA. The DNA is then bound to an intercalating agent as described above, and separated on the analyzer based on relative base content to isolate DNA of interest. Sorted DNA is then used for the generation of gene libraries, which are then screened for activities of interest.

As indicated, one embodiment for forming a normalized library from an environmental sample begins with the isolation of nucleic acid from the sample. This nucleic acid can then be fractionated prior to normalization to increase the chances of cloning DNA from minor species from the pool of organisms sampled. DNA can be fractionated using a density centrifugation technique, such as a cesium-chloride gradient. When an intercalating agent, such as bis-benzimide is employed to change the buoyant density of the nucleic acid, gradients will fractionate the DNA based on relative base content. Nucleic acid from multiple organisms can be separated in this manner, and this technique can be used to fractionate complex mixtures of genomes. This can be of particular value when working with complex environmental samples. Alternatively, the DNA does not have to be fractionated prior to normalization. Samples are recovered from the fractionated DNA, and the strands of nucleic acid are then melted and allowed to selectively reanneal under fixed conditions($C_o t$ driven hybridization). When a mixture of nucleic acid fragments is melted and allowed to reanneal under stringent conditions, the common sequences find their complementary strands faster than the rare sequences. After an optional single-stranded nucleic acid isolation step, single-stranded nucleic acid representing an enrichment of rare sequences is amplified using techniques well known in the art, such as a polymerase chain reaction (Barnes, 1994), and used to generate gene libraries. This procedure leads to the amplification of rare or low abundance nucleic acid molecules, which are then used to generate a gene library which can be screened for a desired bioactivity. While DNA will be recovered, the identification of the organism(s) originally containing the DNA may be lost. This method offers the ability to recover DNA from "unclonable" sources. This method is further detailed in the example below. A.

Hence, one embodiment for forming a normalized library from environmental sample(s) is by (a) isolating nucleic acid from the environmental sample(s); (b) optionally fractionating the nucleic acid and recovering desired fractions; (c) normalizing the representation of the DNA within the population so as to form a normalized expression library from the DNA of the environmental sample(s). The normalization process is described and exemplified in detail in co-pending, commonly assigned U.S. Ser. No. 08/665,565, filed Jun. 18, 1996.

Gene Libraries

Gene libraries can be generated by inserting the normalized or non-normalized DNA isolated or derived from a sample into a vector or a plasmid. Such vectors or plasmids are preferably those containing expression regulatory sequences, including promoters, enhancers and the like. Such polynucleotides can be part of a vector and/or a composition and still be isolated, in that such vector or composition is not part of its natural environment. Particularly preferred phage or plasmids and methods for introduction and packaging into them are described herein.

The examples below detail procedures for producing libraries from both cultured and non-cultured organisms.

Cloning of DNA fragments prepared by random cleavage of the target DNA can also be used to generate a representative library. DNA dissolved in TE buffer is vigorously passed through a 25 gauge double-hubbed needle until the sheared fragments are in the desired size range. The DNA ends are "polished" or blunted with Mung Bean Nuclease, and EcoRI restriction sites in the target DNA are protected with EcoRI Methylase. EcoRI linkers (GGAATTCC SEQ ID No.1) are ligated to the blunted/protected DNA using a very high molar ratio of linkers to target DNA. This lowers the probability of two DNA molecules ligating together to create a chimeric clone. The linkers are cut back with EcoRI restriction endonuclease and the DNA is size fractionated. The removal of sub-optimal DNA fragments and the small linkers is critical because ligation to the vector will result in recombinant molecules that are unpackageable, or the construction of a library containing only linkers as inserts. Sucrose gradient fractionation is used since it is extremely easy, rapid and reliable. Although the sucrose gradients do not provide the resolution of agarose gel isolations, they do produce DNA that is relatively free of inhibiting contaminants. The prepared target DNA is ligated to the lambda vector, packaged using in vitro packaging extracts and grown on the appropriate E. coli.

As representative examples of expression vectors which may be used there may be mentioned viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus, yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used as long as they are replicable and viable in the host. Low copy number or high copy number vectors may be employed with the present invention.

A preferred type of vector for use in the present invention contains an f-factor origin replication. The f-factor (or fertility factor) in E. coli is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from E. coli f-factor which is able to stably integrate large segments of genomic DNA. When integrated with DNA from a mixed uncultured environmental sample, this makes it possible to achieve large genomic fragments in the form of a stable "environmental DNA library."

Another preferred type of vector for use in the present invention is a cosmid vector. Cosmid vectors were originally designed to clone and propagate large segments of genomic DNA. Cloning into cosmid vectors is described in detail in Sambrook, et al., Molecular Cloning A Laboratory Manual, $2^{nd}$ Edition, Cold Spring Harbor Laboratory Press, 1989.

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), -factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The cloning strategy permits expression via both vector driven and endogenous promoters; vector promotion may be important with expression of genes whose endogenous promoter will not function in E. coli.

The DNA derived from a microorganism(s) may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA selected and isolated as hereinabove described is introduced into a suitable host to prepare a library which is screened for the desired activity. The selected DNA is preferably already in a vector which includes appropriate control sequences whereby selected DNA which encodes for a bioactivity may be expressed, for detection of the desired activity. The host cell is a prokaryotic cell, such as a bacterial cell. Particularly preferred host cells are *E.coli*. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)). The selection of an appropriate host is deemed to be within the scope of those skilled in the art from the teachings herein.

Host cells are genetically engineered (transduced or transformed or transfected) with the vectors. The engineered host cells can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

Since it appears that many bioactive compounds of bacterial origin are encoded in contiguous multigene pathways varying from 15 to 100 kbp, cloning large genome fragments is preferred with the present invention, in order to express novel pathways from natural assemblages of microorganisms. Capturing and replicating DNA fragments of 40 to 100 kbp in surrogate hosts such as *E. coli. Bacillus* or *Streptomyces* is in effect propagating uncultivated microbes, albeit in the form of large DNA fragments each representing from 2 to 5% of a typical eubacterial genome.

Two hurdles that must be overcome to successfully capture large genome fragments from naturally occurring microbes and to express multigene pathways from subsequent clones are 1) the low cloning efficiency of environmental DNA and 2) the inherent instability of large clones. To overcome these hurdles, high quality large molecular weight DNA is extracted directly from soil and other environments and vectors such as the f-factor based Bacterial Artificial Chromosome (BAC) vectors are used to efficiently clone and propagate large genome fragments. The environmental library approach will process such samples with an aim to archive and replicate with a high degree of fidelity the collective genomes in the mixed microbial assemblage. The basis of this approach is the application of modified Bacterial Artificial Chromosome (BAC) vectors to stably propagate 100–200 kbp genome fragments. The BAC vector and its derivative, the fosmid (for f-factor based cosmid), use the f-origin of replication to maintain copy number at one or two per cell. This feature has been shown to be a crucial factor in maintaining stability of large cloned fragments. High fidelity replication is especially important in propagating libraries comprised of high GC organisms such as the *Streptomyces* from which clones may be prone to rearrangement and deletion of duplicate sequences.

Because the fosmid vector uses the highly efficient lambda packaging system, comprehensive libraries can be assembled with a minimal amount of starting DNA. environmental fosmid libraries of $4 \times 10^7$ clones of the present invention can be generated, each containing approximately 40 kbp of cloned DNA, from 100 ng of purified DNA collected from samples, including, for example, from the bug traps described herein.

A potential problem with constructing libraries for the expression of bioactive compounds in *E. coli* is that this gram-negative bacterium may not have the appropriate genetic background to express the compounds in their active form. One aspect of the present invention allows the efficient cloning of fragments in *E. coli* and the subsequent transfer to a different suitable host for expression and screening. Shuttle vectors, which allow propagation in two different types of hosts, can be utilized in the present invention to clone and propagate in bacterial hosts, such as *E. coli*, and transfer to alternative hosts for expression of active molecules. Such alternative hosts may include but are not limited to, for example, *Streptomyces* or *Bacillus*, or other metabolically rich hosts such as *Cyanobacteria, Myxobacteria*, etc. *Streptomyces lividans*, for instance, may be used as the expression host for the cloned pathways. This strain is routinely used in the recombinant expression of heterologous antibiotic pathways because it recognized a large number of promoters and appears to lack a restriction system (Guseck, T. W. & Kinsella, J. E., (1992) *Crit. Rev. Microbiol.* 18, 247–260).

In the present invention, the example below describes a shuttle vector which can be utilized. The vector is an *E. coli-Streptomyces* shuttle vector. This system allows one to stably clone and express large inserts (40 kbp genome fragments). Chromosomally integrated recombinants can be recovered as the original fosmid to facilitate sequence characterization and further manipulation of positive clones. Replicons which allow regulation of the clone copy number in hosts can be utilized. For instance, the SPC2 replicon, a 32 kb fertility plasmid that is present at one copy per cell in *Streptomyces coelicolor*, can be utilized. This replicon can be "tuned" by truncation to replicate at various copy number in *Streptomyces* hosts. For instance, replicative versions of integrative shuttle vectors maybe designed containing the full length and truncated SCP2 replicon which will regulate the clone copy number in the *Streptomyces* host from 1 to 10 copies per cell.

In order to ensure that the bioactivity of the clones containing the putative polyketide or other clustered genes is not due to the activation of any resident gene cluster, the resident gene sequences can be removed from the host strain by gene replacement or deletion. An example is presented below.

Biopanning

After the expression libraries have been generated, one can include the additional step of "biopanning" such libraries prior to transfer to a second host for screening. The "biopanning" procedure refers to a process for identifying clones having a specified biological activity by screening for sequence homology in a library of clones prepared by (i) selectively isolating target DNA, from DNA derived from at least one microorganism, by use of at least one probe DNA comprising at least a portion of a DNA sequence encoding an biological having the specified biological activity; and (ii) transforming a host with isolated target DNA to produce a library of clones which are then processed for screening for the specified biological activity.

The procedure of "biopanning" is described and exemplified in U.S. Ser. No. 08/692,002, filed Aug. 2, 1996, now U.S. Pat. No. 6,054,267.

Further, it is possible to combine all the above embodiments such that a normalization step is performed prior to generation of the expression library, the expression library is then generated, the expression library so generated is then biopanned, and the biopanned expression library is then screened using a high throughput cell sorting and screening instrument. Thus there are a variety of options: i.e. (i) one can just generate the library and then screen it; (ii) normalize the target DNA, generate the expression library and screen it; (iii) normalize, generate the library, biopan and screen; or (iv) generate, biopan and screen the library.

Screening

The present invention offers the ability to screen for many types of bioactivities, in particular bioactivities which are enhancers and inhibitors of protein-protein or other interactions, such as those between transcription factors and their activators, or receptors and their cognate targets.

The biopanning approach described above can be used to create libraries enriched with clones carrying sequences homologous to a given probe sequence. Using this approach libraries containing clones with inserts of up to 40 kbp can be enriched approximately 1,000 fold after each round of panning. This enables one to reduce the above 3,000 filter fosmid library to 3 filters after 1 round of biopanning enrichment. This approach can be applied to create libraries enriched for clones carrying desirable sequences.

Hybridization screening using high density filters or biopanning has proven an efficient approach to detect homologues of pathways containing conserved genes. To discover novel bioactive molecules that may have no known counterparts, however, other approaches are necessary.

Thus, one aspect of the present invention provides a method for detecting molecules which effect the interaction between a first protein and a second protein, or between two or more molecules. Molecules to be evaluated may be encoded for by one or more genes, or may include other molecules not encoded for by nucleic acids, including nucleic acids themselves or other molecules generated via, for example, combinatorial chemistry technologies. Such molecules would include, natural or synthesized peptides, natural products and synthesized products.

Prokaryotic or eukaryotic hosts may be utilized with the method of the present invention. The host cell may contain a detectable gene having a binding site for the DNA-binding domain of a transcriptional activator, such that the detectable gene expresses a detectable protein when the detectable gene is transcriptionally activated. Such activation occurs when the transcriptional activation domain of a transcriptional activator is brought into sufficient proximity to the DNA-binding domain of the transcriptional activator. Alternatively, the host cell contain a detectable gene having a binding site for a binding domain of a transcriptional repressor, such that the detectable gene expresses when the repressor is not bound. Such repression occurs when the domains of the repressor are brought into sufficient proximity to each other. Alternatively, interacting molecules can be fused or associated with other molecules, which, when brought in sufficient proximity to each other, generate a detectable signal.

In one aspect of the present invention, a first chimeric gene is provided which is capable of being expressed in the host cell. The first chimeric gene comprises a DNA sequence that encodes a first hybrid protein. The first hybrid protein contains either a DNA-binding domain that recognizes the binding site near the detectable gene in the host cell, or a molecule which when brought into sufficient proximity to the molecule on a second hybrid protein, generates a detectable signal. The first hybrid protein also contains a first protein or protein fragment which is to be interacted with a second protein or protein fragment. The first chimeric gene may be present in a chromosome of the host cell, or it may be encoded on a library of plasmids or other vectors that contain genomic, cDNA or synthetically generated DNA sequences fused to the DNA sequence encoding the DNA-binding domain.

A second chimeric gene is provided which is capable of being expressed in the host cell. In one embodiment, both the first and the second chimeric genes are introduced into the host cell in the form of plasmids or other vectors. In another embodiment, the first chimeric gene is present in a chromosome of the host cell and the second chimeric gene is introduced into the host cell as part of a plasmid or other type of vector. The second chimeric gene contains a DNA sequence that encodes a second hybrid protein. The second hybrid protein contains a transcriptional activation domain which when interacted with the binding domain and the operator or other sequence near the detectable gene in the host cell, causes transcriptional activation of the detectable gene. Alternatively, the second hybrid protein contains a dimerization or other domain ("transcriptional repressor") which when interacted with the binding domain and the operator or other sequence near the detectable gene in the host cell, causes transcriptional repression of the detectable gene. Alternatively, the second hybrid protein contains a molecule which when brought into sufficient proximity to the molecule on a first hybrid protein, generates a detectable signal. The second hybrid protein also contains a second protein or a protein fragment which is to be tested for interaction with the first protein or protein fragment. Preferably, the DNA-binding domain of the first hybrid protein and the transcriptional activation domain or transcriptional repressor of the second hybrid protein are derived from transcriptional activators or repressors having separate DNA-binding and transcriptional activation domains or dimerization or other domains as described above. Many proteins involved in transcription have separable binding and transcriptional activation or "repressor" (as described above) domains which make them useful for the present invention. In another embodiment, the DNA-binding domain and the transcriptional activation or dimerization or other domain (as described above) may be from different transcriptional activators or repressors. The second hybrid protein may be encoded on a library of plasmids or other vectors that contain genomic, cDNA or synthetically generated DNA sequences fused to the DNA sequence encoding the transcriptional activation domain or transcriptional repressor.

Alternatively, in the method of the present invention, a first test protein associated with a DNA-binding domain and a second test protein associated with a transcriptional activator or repressor may also be introduced into the cell as protein products instead of as genes as described above. Said associated proteins may be generated or synthesized in vitro or in vivo, and protein products may be introduced into the host cell for screening utilizing the methods of the present invention. If activators or repressors are not employed to activate or repress the expression of a detectable gene, the first test protein and the second test protein can be associated with molecules which generate a detectable signal when they are brought into sufficient proximity to each other, and introduced into host cells to be screened using the methods of the present invention.

Therefore, in the case of the utilization of a transcriptional activator, interaction between the first protein and the second protein in the host cell, causes the transcriptional activation domain to activate transcription of the detectable gene. The method is carried out by introducing the first chimeric gene and the second chimeric gene into the host cell. The host cell is subjected to conditions under which the first hybrid protein and the second hybrid protein are expressed in sufficient quantity for the detectable gene to be activated. The cells are then tested for their expression of the detectable gene to a greater degree than in the absence of an interaction between the first protein and the second protein. A third gene or gene cluster is then introduced into the host cell, and an enhancement or inhibition of the interaction of the first and second proteins is evaluated by increased or decreased expression of the detectable gene. Enhancement of the interaction between the first and second protein could yield an increase in expression of the detectable gene, while inhibition of the interaction between the first and second protein would yield a decrease in expression of the detectable gene. The third gene or gene cluster can also be introduced into the cell prior to the introduction of the first and/or second gene, or simultaneously with the first and/or second gene. Alternatively, the molecule to be evaluated for its effect on the interaction of the first two proteins can be introduced directly into the host cell not in the form of a gene or gene cluster, but as a product.

In the case of the utilization of a transcriptional repressor, interaction between the first protein and the second protein in the host cell, causes the transcriptional repression domain to repress transcription of the detectable gene. The method is carried out by introducing the first chimeric gene and the second chimeric gene into the host cell. The host cell is subjected to conditions under which the first hybrid protein and the second hybrid protein are expressed in sufficient quantity for the detectable gene to be inactivated. The cells are then tested for their lack of expression of the detectable gene. A third gene or gene cluster is then introduced into the host cell, and an inhibition of the interaction between the first and second protein results in an increase in expression of the detectable gene. Again, the third gene or gene cluster can be introduced into the cell prior to the introduction of the first and/or second gene, or simultaneously with the first and/or second gene, and the molecule to be evaluated for its effect on the interaction of the first two proteins can be introduced directly into the host cell not in the form of a gene or gene cluster, but as a product.

In the case of the utilization of molecules which can associate when in proximity to each other to generate a detectable signal, interaction between the first protein and the second protein in the host cell causes a detectable signal to be generated. The method is carried out by introducing the first chimeric gene and the second chimeric gene into the host cell. The host cell is subjected to conditions under which the first hybrid protein and the second hybrid protein are expressed in sufficient quantity for the detectable signal to be generated. The cells are then tested for the presence of the detectable signal. A third gene or gene cluster is then introduced into the host cell, and an enhancement or inhibition of the interaction between the first and second protein results in an increase or decrease in detectable signal. Again, the third gene or gene cluster can be introduced into the cell prior to the introduction of the first and/or second gene, or simultaneously with the first and/or second gene, and the molecule to be evaluated for its effect on the interaction of the first two proteins can be introduced directly into the host cell not in the form of a gene or gene cluster, but as a product.

Thus, enhancement or inhibition of interactions between a first protein and a second protein by a library of third test proteins or molecules can be tested. For example, the first and second proteins may be derived from bacteria, or viruses, and/or may be an oncogene-encoded protein, a growth factor or an enzyme. The third protein may be derived from a gene library described herein or may be any molecule desired to be screened for its potential to effect the interaction of other molecules.

The screening aspect of the present invention may be practiced using three vectors and a host cell. The first vector contains a promoter and may include a transcription termination signal functionally associated with the first chimeric gene in order to direct the transcription of the first chimeric gene. The first chimeric gene includes a DNA sequence that encodes a DNA-binding domain and a unique restriction site(s) for inserting a DNA sequence encoding a first protein or protein fragment in such a manner that the first protein is expressed as part of a hybrid protein with the DNA-binding domain. The first vector also includes a means for replicating itself in the host cell. Also included on the first vector is a first marker gene, the expression of which in the host cell permits selection of cells containing the first marker gene from cells that do not contain the first marker gene. Preferably, the first vector is a phage, cosmid, plasmid, phagemid, or fosmid or other BAC vector.

The second vector will contain a second chimeric gene. The second chimeric gene also includes a promoter and a transcription termination signal to direct transcription. The second chimeric gene also includes a DNA sequence that encodes a transcriptional activation domain and a unique restriction site(s) to insert a DNA sequence encoding the second protein or protein fragment into the vector, in such a manner that the second protein is capable of being expressed as part of a hybrid protein with the transcriptional activation domain. Preferably, the DNA-binding domain of the first hybrid protein and the transcriptional activation domain of the second hybrid protein are derived from transcriptional activators having separate DNA-binding and transcriptional activation domains. Many proteins involved in transcription have separable binding and transcriptional activation domains which make them useful for the present invention. In another embodiment, the DNA-binding domain and the transcriptional activation domain may be from different transcriptional activators. The second hybrid protein may be encoded on a library of vectors that contain genomic, cDNA or synthetically generated DNA sequences fused to the DNA sequence encoding the transcriptional activation domain.

Alternatively, the second chimeric gene includes instead a DNA sequence that encodes a transcriptional repression domain, and a unique restriction site(s) to insert a DNA sequence encoding the second protein or protein fragment into the vector, in such a manner that the second protein is capable of being expressed as part of a hybrid protein with the transcriptional repression domain. Preferably, the DNA-binding domain of the first hybrid protein and the transcriptional repression domain of the second hybrid protein are derived from transcriptional repressors having separate DNA-binding and transcriptional repression domains. Many proteins involved in transcription have separable binding and transcriptional repression domains which make them useful for the present invention. In another embodiment, the DNA-binding domain and the transcriptional repression domain may be from different transcriptional repressors. The second hybrid protein may be encoded on a library of vectors that contain genomic, cDNA or synthetically generated DNA sequences fused to the DNA sequence encoding the transcriptional repression domain.

The second vector further includes a means for replicating itself in the host cell. The second vector also includes a second marker gene, the expression of which in the host cell permits selection of cells containing the second marker gene from cells that do not contain the second marker gene.

The third vector contains a promoter and may include a transcription termination signal functionally associated with the third gene or gene cluster in order to direct the transcription of the third gene or gene cluster. The third vector includes a unique restriction site(s) for inserting a DNA sequence encoding a third protein, group of proteins (for example, those encoded by a gene cluster) or protein fragment. The third vector also includes a means for replicating itself in the host cell and in bacteria. The third vector can also include a third marker gene, the expression of which in the host cell permits selection of cells containing the third marker gene from cells that do not contain the third marker gene. Preferably, the third vector is a phage, cosmid, plasmid, phagemid, or fosmid or other BAC vector.

Alternatively, the screening aspect of the present invention is not practiced using vectors, but rather using interacting hybrid molecules associated with DNA-binding domains and transcriptional activators or repressors, or with other molecules which generate a detectable signal when brought into sufficient proximity to each other, and a host cell.

The host cell is a eukaryotic or a prokaryotic cell. The host cell contains the detectable gene having a binding site for the DNA-binding domain of the first hybrid protein. The binding site is positioned so that the detectable gene expresses a detectable protein when the detectable gene is activated by the transcriptional activation domain encoded by the second vector. Activation of the detectable gene is possible when the transcriptional activation domain is in sufficient proximity to the detectable gene. Alternatively, in the case of the utilization of a transcriptional repressor, the repressor binding site is positioned so that the detectable gene does not express the detectable protein when the detectable gene is repressed by the transcriptional repression domain encoded by the second vector. Repression of the detectable gene is possible when the transcriptional repression domain is in sufficient proximity to the detectable gene. Alternatively, in the case of the use of other associating molecules which associate to generate a detectable signal, no detectable gene is present in the host cell. The host cell, by itself, is incapable of expressing a protein having a function of the first marker gene, the second marker gene, the DNA-binding domain, the transcriptional activation domain, or the molecules capable of associating to generate a detectable signal. The DNA binding domain and the transcriptional activation or repression domain, and the associating molecules in the latter case, are incapable of interacting with each other unless the first and second proteins bring them together by their interaction.

Accordingly, in the case of the utilization of a transcriptional activator, the interaction of the first protein and the second protein in the host cell causes a measurably greater expression of the detectable gene than when the DNA-binding domain and the transcriptional activation domain are present, in the absence of an interaction between the first protein and the second protein. Alternatively, in the case of the utilization of a transcriptional repressor, the interaction of the first protein and the second protein in the host cell causes repression of expression of the detectable gene.

The detectable gene may encode an enzyme or other product that can be readily measured. Such measurable activity may include the ability of the cell to grow only when the marker gene is transcribed, or the presence of detectable enzyme activity only when the marker gene is transcribed. Various other markers are well known by the skilled artisan.

Fluorescent indicators which interact when associated to create a detectable signal may be utilized in the method of the present invention. For example, green fluorescent protein (GFP) mutants can be generated which have increased fluorescence resonance energy transfer between flanking GFP's. Thus fluorescence resonance energy can be transferred and measured upon association of mutant GFP molecules. First test proteins associated with one GFP mutant, and second test proteins associated with another test mutant can come together and an energy transfer can occur and be measured via the association of the two GFP molecules. Hybrid molecules are structured such that GFP mutants are not interacting independently, but only upon interaction of the proteins or molecules associated with the mutants. Third molecules can then be evaluated for their capability to affect the interaction of the first two molecules.

The cells containing the two hybrid proteins are incubated in an appropriate medium and the culture is monitored for the measurable activity. In the case of the utilization of a transcriptional activator, a positive indication that the first protein and the second protein have interacted is expression of the detectable gene. Such interaction brings their respective DNA-binding and transcriptional activation domains into sufficiently close proximity to cause transcription of the marker gene. In the case of the utilization of a transcriptional repressor, a positive indication that the first protein and the second protein have interacted is repression of expression of the detectable gene. Such interaction brings their respective DNA-binding and transcriptional repression domains into sufficiently close proximity to cause repression of transcription of the marker gene. In the case where two molecules are coming together in close enough proximity to generate a detectable signal, a positive indication that the first and second molecules have interacted is detection of the signal.

The third vector containing the third gene or gene cluster encoding a third protein or group of proteins is introduced into the cells containing the two hybrid proteins which are interacting. Alternatively, the third protein or other molecule is introduced directly into the cells containing the two hybrid proteins which are interacting. Expression of a third protein or group of proteins, or the presence of a third molecule which inhibits or enhances the interaction of the first and second proteins yields a measurable difference in expression of the detectable gene. Such difference is evaluated by detection of the amount of detectable molecules produced by the detectable gene. In the case of the utilization of a transcriptional activator, inhibition of the interaction between the two proteins results in a decrease in the expression levels of the detectable molecule and enhancement of the interaction between the two proteins results in an increase in the expression levels of the detectable molecule. In the case of the utilization of a transcriptional repressor, inhibition of the interaction between the two proteins results in an increase in the expression levels of the detectable molecule. Enhancement or inhibition of the interaction between the first two proteins in the case of the utilization of associating molecules which generate a detectable signal results in a decrease or increase in the detectable signal, respectively.

The system is dependent on a number of conditions to properly carry out the method of this invention. The first interacting protein X must not itself, carry an activation or repression domain for the marker. Otherwise the activation domain would allow transcription or repress transcription of the marker gene as soon as the vector encoding only the DNA-binding domain fused to the first interacting protein X is introduced. The interaction between the first protein X and the second protein Y must be capable of occurring within the host cell. The activation domain portion of the hybrid containing the second protein Y must be accessible to the transcription machinery of the cell to allow transcription of the marker gene. In the case of the utilization of a transcriptional repressor, the detectable gene should be expressing in the absence of the interaction of the two hybrid proteins. Should any of these conditions not exist, the system may be modified for use by constructing hybrids that carry only portions of the interacting proteins X and Y and thus meet these conditions.

This system can be used to select generically for proteins or groups of proteins that inhibit or enhance the interaction of other proteins or molecules. Prokaryotes containing a known protein as a hybrid with the DNA-binding domain can be transformed with a clone bank of genomic or cDNA sequences fused to the activation or repression domain. The double transformants can be screened for expression of the detectable marker. The third protein or group of proteins can then be introduced and expressed. Inhibition or enhancement of the interaction between the first and second proteins can then be evaluated.

Since prokaryotes use similar transcription mechanisms, a variety of cells can be used to test for protein-protein interactions. The reporter gene function can be served by any of a large variety of genes, such as genes encoding drug resistance or metabolic enzymes. Any transcriptional activator or repressor that has separable domains for DNA-binding and for transcriptional activation or repression can be employed. Indeed, any protein, even one that is not a transcriptional activator or repressor, that has two separable functions can be used to establish a similar genetic system to detect enhancement or inhibition of protein-protein or other interactions.

Accordingly, the method of the present invention can be applied more generally to utilize any detectable function requiring separable domains of an amino acid sequence which can be reconstituted. This general embodiment of the present invention detects inhibition or enhancement of the interaction between a first protein and a second protein. The method includes providing a host cell which is defective in a detectable function. The detectable function is provided by an amino acid sequence having separable domains. Thus, the amino acid sequence includes a first domain and a second domain which are capable of producing the detectable function when they are in sufficient proximity to each other in the host cell.

A first chimeric gene is provided that is capable of being expressed in the host cell. The first chimeric gene includes a DNA sequence that encodes a first hybrid protein. The first hybrid protein contains the first domain of the amino acid sequence. The first hybrid protein also contains a first protein or protein fragment which is to be interacted with a second protein or protein fragment.

A second chimeric gene is provided which is capable of being expressed in the host cell. The second chimeric gene contains a DNA sequence that encodes a second hybrid protein. The second hybrid protein contains the second domain of the amino acid sequence. The second hybrid protein also contains a second protein or protein fragment which is to be interacted with a first protein or protein fragment.

The interaction between the first protein and the second protein in the host cell, causes the function of the amino acid sequence to be reconstituted. The method is thus carried out by introducing the first chimeric gene and the second chimeric gene into the host cell. The host cell is subjected to conditions under which the first hybrid protein and the second hybrid protein are expressed in sufficient quantity for the function of the amino acid sequence to be reconstituted. The cells are then tested to determine whether their expression of the function of the amino acid sequence has been reconstituted to a degree greater than in the absence of the interaction of the test proteins. The third vector encoding a third protein or group of proteins is then untroduced into the host cell. A protein or group of proteins which enhance or inhibit the interaction of the first and second proteins is then determined by evaluating expression levels of a detectable gene.

This generalized method can be made more specific, for example, as described for the preferred method of the present invention in which the detectable function is transcription of a detectable gene or repression of transcription of a detectable gene. In this method, the first domain of the amino acid sequence includes a DNA-binding domain that recognizes a binding site on the detectable gene, and the second of the amino acid sequence includes a transcriptional activation or repression domain.

In the generalized method, described above, the host cell is prokaryotic or eukaryotic cell. In carrying out this method, the first and/or second proteins may be derived from a bacterial protein, a viral protein, an oncogen-encoded protein, a growth factor or an enzyme. The second hybrid protein may also be encoded on a library of plasmids containing DNA inserts that are derived from genomic DNA, cDNA, or synthetically generated DNA sequences fused to the DNA sequence encoding the second amino acid domain. The third protein or group of proteins may be encoded on a library of plasmids containing DNA inserts that are derived from genomic DNA, cDNA, or synthetically generated DNA sequences fused to the DNA sequence encoding the third amino acid domain.

The method of the present invention may also be utilized to evaluate the inhibition or enhancement of interaction of molecules other than proteins. Interacting molecules can be fused to the separate domains (DNA-binding domains and transcriptional activation or repression domains) of transcriptional activators or repressors. Typically, transcriptional activators or repressors are proteins. Alternatively, interacting molecules can be fused to molecules which, when brought into sufficient proximity to each other, can generate a detectable signal. Certain linkers for linking or associating two or more molecules together, and/or for linking molecules to proteins are known in the art Linkage or association of interacting molecules to these domains or molecules, yields hybrid molecules that, upon interaction of the two interacting molecules, are capable of activating or repressing expression of a detectable gene, or generating a detectable signal themselves, as described above. The hybrid molecules are introduced into host cells. A library of third proteins or group of proteins are then introduced into the same host cells, either by introduction of the gene encoding the protein or genes encoding these proteins, or by introduction of the proteins themselves, or of molecules generated via expression of the multiple proteins (for example, the molecules generated via expression of a gene cluster or pathway), or of molecules desired to be evaluated, such as molecules generated via combinatorial chemistry technologies. Enhancement or inhibition of the interaction between the interacting molecules can then be evaluated by the effects on gene expression of the detectable molecule, or presence of the detectable molecule, as described above.

FACS screening of clones using the methods of the present invention can be performed as described in U.S. patent application Ser. No. 08/876,276, filed Jun. 16, 1997. Other devices which utilize detectors capable of detecting any detectable molecule utilized in a method of the present invention may be employed. Such devices include, but are not limited to, a variety of high throughput cell sorting instruments, robotic instruments, and time-resolved fluorescence instruments, which can actually measure the fluorescence from a single molecule over an elapsed period of time.

Recovering Desirable Bioactivities

After screening, positive clones, in the case where recombinant DNA potentially encoding activities of interest is utilized, are recovered, and DNA is isolated from positive clones utilizing techniques well known in the art. The DNA can then be amplified either in vivo or in vitro by utilizing any of the various amplification techniques known in the art. In vivo amplification would include transformation of the clone(s) or subclone(s) of the clones into a viable host, followed by growth of the host. In vitro amplification can be performed using techniques such as the polymerase chain reaction.

The clones which are identified as having the specified activity may then be sequenced to identify the DNA sequence encoding a bioactivity having the specified activity. Thus, in accordance with the present invention it is possible to isolate and identify: (i) DNA encoding a bioactivity having a specified activity, (ii) bioactivities having such activity (including the amino acid sequence thereof) and (iii) produce recombinant molecules having such activity.

Evolution

One advantage afforded by a recombinant approach to the discovery of novel bioactive compounds is the ability to manipulate pathway subunits to generate and select for variants with altered specificity. Pathway subunits can be substituted or individual subunits can be evolved utilizing methods described below, to select for resultant bioactive molecules with different activities.

Clones found to have the bioactivity for which the screen was performed can be subjected to directed mutagenesis to develop new bioactivities with more desirable properties or to develop modified bioactivities with particularly desired properties that are absent or less pronounced in the wild-type activity, such as stability to heat or organic solvents. Any of the known techniques for directed mutagenesis are applicable to the invention. For example, particularly preferred mutagenesis techniques for use in accordance with the invention include those described below.

The term "error-prone PCRI" refers to a process for performing PCR under conditions where the copying fidelity of the DNA polymerase is low, such that a high rate of point mutations is obtained along the entire length of the PCR product. Leung, D. W., et al., Technique, 1:11–15 (1989) and Caldwell, R. C. & Joyce G. F., PCR Methods Applic., 2:28–33 (1992).

The term "oligonucleotide directed mutagenesis" refers to a process which allows for the generation of site-specific mutations in any cloned DNA segment of interest. Reidhaar-Olson, J. F. & Sauer, R. T., et al., Science, 241:53–57 (1988).

The term "assembly PCR" refers to a process which involves the assembly of a PCR product from a mixture of small DNA fragments. A large number of different PCR reactions occur in parallel in the same vial, with the products of one reaction priming the products of another reaction.

The term "sexual PCR mutagenesis" (also known as "DNA shuffling") refers to forced homologous recombination between DNA molecules of different but highly related DNA sequence in vitro, caused by random fragmentation of the DNA molecule based on sequence homology, followed by fixation of the crossover by primer extension in a PCR reaction. Stemmer, W. P., PNAS, USA, 91:10747–10751 (1994).

The term "in vivo mutagenesis" refers to a process of generating random mutations in any cloned DNA of interest which involves the propagation of the DNA in a strain of *E. coli* that carries mutations in one or more of the DNA repair pathways. These "mutator" strains have a higher random mutation rate than that of a wild-type parent. Propogating the DNA in one of these strains will eventually generate random mutations within the DNA.

The term "cassette mutagenesis" refers to any process for replacing a small region of a double stranded DNA molecule with a synthetic oligonucleotide "cassette" that differs from the native sequence. The oligonucleotide often contains completely and/or partially randomized native sequence.

The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Arkin, A. P. and Youvan, D. C., PNAS, USA, 89:7811–7815 (1992).

The term "exponential ensemble mutagenesis" refers to a process for generating combinatorial libraries with a high percentage of unique and functional mutants, wherein small groups of residues are randomized in parallel to identify, at each altered position, amino acids which lead to functional proteins, Delegrave, S. and Youvan, D. C., Biotechnology Research, 11:1548–1552 (1993); and random and site-directed mutagenesis, Arnold, F. H., Current Opinion in Biotechnology, 4:450–455 (1993).

All of the references mentioned above are hereby incorporated by reference in their entirety. Each of these techniques is described in detail in the references mentioned.

DNA encoding desirable molecules identified utilizing the methods of the present invention can be mutagenized, or "evolved", utilizing any one or more of these techniques, and rescreened utilizing the methods of the present invention to identify more desirable clones.

The invention will now be illustrated by the following working examples, which are in no way a limitation thereof.

Example 1

Sample Collection

Sample to be utilized for downstream nucleic acid isolation for library generation may be collected according to the following example:

The following represents a method of selective in situ enrichment of bacterial and archaeal species while at the same time inhibiting the proliferation of eukaryotic members of the population.

In situ enrichment is achieved by using traps composed of growth substrates and nutritional amendments with the intent to lure, selectively, members of the surrounding environmental matrix, coated onto surfaces. Choice of substrates (carbon sources) and nutritional amendments (ie, nitrogen, phosphorous, etc.) is dependent upon the members of the community one desires to enrich. Selective agents against eukaryotic members are also added to the trap. Again, the exact composition will depend upon which members of the community one desires to enrich and which members of the community one desires to inhibit. Substrates include monomers and polymers. Monomers of substrates, such as glucosamine, cellulose, pentanoic or other acids, xylan, chitin, etc., can be utilized for attraction of certain types of microbes. Polymers can also be used to attract microbes that can degrade them. Some of the enrichment media which may be useful in pulling out particular members of the community is described below:

1. Addition of bioactive compounds against fungi and microscopic eukaryotes:

Proliferation of eukaryotic members of the community may be inhibited by the use of one or more commercially available compounds such as nystatin, cycloheximide, and/or pimaricin. These compounds may be sprinkled as a powder or incorporated as a liquid in the bug trap medium.

2. Addition of bioactive compounds against other bacterial species:

Compounds which inhibit the growth of some bacterial species but not others (ie, polymyxin, penicillin, and rifampin) may be incorporated into the enrichment medium. Use of the compounds is dependent upon which members of the bacterial community one desires to enrich. For example, while a majority of the *Streptomyces* are sensitive to polymyxin, penicillin, and rifampin, these may be used to enrich for rare members of the family which are resistant. Selective agents may also be used in enrichments for archaeal members of the community.

3. Use of carbon sources as selective agents:

Any particular carbon source can be utilized by some members of the community and not others. Carbon source selection thus depends upon the members of the community one desires to enrich. For example, members of the *Streptomycetales* tend to utilize complex, polymeric substrates such as cellulose, chitin, and lignin. These complex subtrates, while utilized by other genera, are recalcitrant to most bacteria. These complex substrates are utilized by fungi, which necessitates the use of anti-fungal agents, mentioned above.

4. Addition of nitrogen sources:

The use of additional nitrogen sources may be called for depending upon the choice for carbon source. For example, while chitin is balanced in its C:N ratio, cellulose is not. To enhance utilization of cellulose (or other carbon-rich substrates), it is often useful to add nitrogen sources such as nitrate or ammonia.

5. Addition of trace elements:

In general, the environmental matrix tends to be a good source of trace elements, but in certain environments, the elements may be limiting. Addition of trace elements may enhance growth of some members of the community while inhibiting others. Large surface area materials, such as glass beads or silica aerogels can be utilized as surfaces in the present example. This allows a high concentration of microbes to be collected in a relatively small device holding multiple collections of substrate-surface conjugates.

Glass beads can be derivitized with N-Acetyl B-D-glucosamine-phenylisothiocyanate as follows:

Bead Preparation 30 milliliters (ml) glass beads (Biospec Products. Bartlesville. Okla.) are mixed with 50 ml APS/Toluene (10% APS) (Sigma Chemical Co.)

Reflux overnight

Decant and wash 3 times with Toluene

Wash 3 times with ethanol and dry in oven

Derivitize with N-Acetyl B-D-glucosamine-phenylisothiocyanate as follows

Combine in Falcon Tube:

25 ml prepared glass beads from above 15 ml 0.1M NaHCO3+25 milligrams (mg) N-Acetyl-B-d-glucosamine-PITC (Sigma Chemical Co.)+1 ml DMSO Add 10 ml NaHCO3+1 ml DMSO Pour over glass beads Let shake in Falcon Tube overnight Wash with 20 ml 0.1M NaHCO3

Wash with 50 ml ddH2O

Dry at 55° C. for 1 hour

Beads can then be placed in mesh filter "bags" (Spectrum, Houston, Tex.) created to allow containment of the beads, while simultaneously allowing migration of microbes, which are then placed in any device used as a solid support which allows containment of the bag. Particularly preferred devices are made of inert materials, such as plexiglass. Alternatively, beads can be placed directly into Falcon Tubes (VWR, Fisher Scientific) which have been punctured with holes using a needle. These "containment" devices are then deployed in desired biotopes for a period of time to allow attraction and growth of desirable microbes.

The following protocol details one method for generating a simple "bug trap":

Puncture holes using a heated needle or other pointed device into a 15 ml Falcon Tube (VWR, Fisher Scientific).

Place approximately 1–5 mls of the derivitized beads into a Spectra/mesh nylon filter, such as those available from Spectrum (Houston, Tex.) with a mesh opening of 70 μm, an open area of 43%, and a thickness of 70 μm. Seal the nylon filter to create a "bag" containing the bends using, for instance, Goop, Household Adhesive & Sealant.

Example 2

DNA Isolation and Library Construction from Cultivated Organism

The following outlines the procedures used to generate a gene library from an isolate, *Streptomnyces rimosus*.

Isolate DNA.

1. Inoculate 25 ml Trypticase Soy Broth (BBL Microbiology Systems) in 250 ml baffled erlenmeyer flasks with spores of *Streptomyces rimosus*. Incubate at 30° C. at 250 rpm for 48 hours.

2. Collect mycelin by centrifugation. Use 50 ml conical tubes and centrifuge at 25° C. at 4000 rpm for 10 minutes.

3. Decant supernatent and wash pellet 2× with 10 ml 10.3% sucrose (centrifuge as above between washes).

4. Store pellet at −20° C. for future use.

5. Resuspend pellet in 40 ml TE (10 mM Tris, 1 mM EDTA; pH 7.5) containing ysozyme (1 mg/ml; Sigma Chemical Co.) and incubate at 37° C. for 45 minutes.

6. Add sarcosyl (N-lauroylsarcosine, sodium salt, Sigma Chemical Co.) to final concentration of 1% and invert gently to mix for several minutes.

7. Transfer 20 ml of preparation to clean tube and add proteinase K (Stratagene Cloning Systems) to a final concentration of 1 mg/ml. Incubate overnight at 50° C.

8. Extract 2× with Phenol (saturated with TE).

9. Extract 1× with Phenol:CH$_3$Cl.

10. Extract 1× with CH$_3$Cl:Isoamyl alcohol.

11. Precipitate DNA with 2 volumes of EtOH.

12. Spool DNA on sealed pasteur pipet.

13. Rinse with 70% EtOH.

14. Dry in air.

15. Resuspend DNA in 1 ml TE and store at 4° C. to rehydrate slowly.

16. Check quality of DNA:

A. Digest 10 μl DNA with EcoRI restriction enzyme (Strategene Cloning Systems) according to manufacturers protocol electrophorese DNA digest through 0.5% agarose 20V overnight: stain gel in 1 μg/ml EtBr.

1. Determine DNA concentration ($A_{260}-A_{280}$).

Restriction Digest DNA

1. Incubate the following at 37° C. for 3 hours:

8 µl DNA (~10 µg)

35 µl H$_2$O

5 µl 10× restriction enzyme buffer

2 µl EcoRI restriction enzyme (200 units)

2. Examine on agarose minigel.

Sucrose Gradient

1. Prepare small sucrose gradient (Sambrook, Fritsch and Maniatus, 1989) and run DNA at 45,000 rpm for 4 hours at 25° C.

2. Examine 5 µl of each fraction on 0.8% agarose gel.

3. Pool relevant fractions and precipitate DNA with 2.5 volumes of EtOH for 1 hour at −70° C.

4. Collect DNA by centrifugation at 13,200 rpm for 15 minutes.

5. Decant and wash with 1 ml of 70% EtOH.

6. Dry, resuspend in 15 µl 5T 1E.

7. Store at 4° C.

Dephosphorylate DNA

I. Dephosphorylate DNA with shrimp alkaline phosphatase according to manufacturers protocol (US Biochemicals).

Adaptor Ligation

I. Ligate adaptors according to manufacturers protocol.

Briefly, gently resuspend DNA in EcoR I-BamH I adaptors (Stratagene Cloning Systems); add 10× ligation buffer, 10 mM rATP, and T4 DNA ligase and incubate at room temperature for 4–6 hours.

Preparation of Fosmid Arms

1. Fosmid arms can be prepared as described (Kim, et.al., Nucl. Acids Res., 20:10832–10835, 1992). Plasmid DNA can be digested with PmeI restriction enzyme (New England Biolabs) according to the manufacturers protocol, dephosphorylated (Sambrook, Fritsch and Maniatus, 1989), followed by a digestion with BamH I restriction enzyme (New England Biolabs) according to the manufacturers protocol, and another dephosphorylation step to generate two arms each of which contain a cos site in the proper orientation for the cloning and packaging of ligated DNA between 35–45 kbp. A.

Ligation to Fosmid Arms

1. Prepare the ligation reaction:

A. Add ~50 nanograms (ng) each of insert and vector DNA to 1U of T4 DNA ligate (Boehringer Mannheim) and 10× ligase buffer as per manufacturers instructions: add H$_2$O if necessary, to total 10 µl.

1. Incubate overnight at 16° C.

Package and Plate

I. Package the ligation reactions using Gigapack XL packaging system (Stratagene Cloning Systems, Inc.) following manufacturer's protocol.

II. Transfect E.coli strain DH10B (Bethesda Research Laboratories, Inc.) according to manufacturers protocol and spread onto LB/Chloramphenicol plates (Sambrook, Fritsh and Maniatus, 1989).

Example 3

Preparation of an Uncultivated Prokaryotic DNA Library

FIG. 1 shows an overview of the procedures used to construct an environmental library from a mixed picoplankton sample. The goal was to construct a stable, large insert DNA library representing picoplankton genomic DNA.

Cell collection and preparation of DNA. Agarose plugs containing concentrated picoplankton cells were prepared from samples collected on an oceanographic cruise from Newport, Oreg. to Honolulu, Hi. Seawater (30 liters) was collected in Niskin bottles, screened through 10 µm Nitex, and concentrated by hollow fiber filtration (Amicon DC10) through 30,000 MW cutoff polysulfone filters. The concentrated bacterioplankton cells were collected on a 0.22 µm. 47 mm Durapore filter, and resuspended in 1 ml of 2× STE buffer (1M NaCl, 0.1M EDTA, 10 mM Tris, pH 8.0) to a final density of approximately $1\times10^{10}$ cells per ml. The cell suspension was mixed with one volume of 1% molten Seaplaque LMP agarose (FMC) cooled to 40° C. and then immediately drawn into a 1 ml syringe. The syringe was sealed with parafilm and placed on ice for 10 mm. The cell-containing agarose plug was extruded into 10 ml of Lysis Buffer(10 mM Tris pH8.0, 50 mM NaCl, 0.1M EDTA, 1% Sarkosyl, 0.2% sodium deoxycholate, a mg/ml lysozyme) and incubated at 37° C. for one hour. The agarose plug was then transferred to 40 mls of ESP Buffer (1% Sarcosyl, 1 mg/ml proteinase-K, in 0.5M EDTA), and incubated at 55° C. for 16 hours. The solution was decanted and replaced with fresh ESP Buffer, and incubated at 55° C. for an additional hour. The agarose plugs were then placed in 50 mM EDTA and stored at 4° C. shipboard for the duration of the oceanographic cruise.

One slice of an agarose plug seventy-two microliters (72l) prepared from a sample collected off the Oregon coast was dialyzed overnight at 4° C. against 1 ml of buffer A (100 mM NaCl, 10 mM Bis Tris Propane-HCl, 100 µg/ml acetylated BSA: pH 7.0 @ 25° C.) in a 2 mL microcentrifuge tube. The solution was replaced with 250 µl of fresh buffer A containing 10 mM MgCl$_2$ and 1 mM DTT and incubated on a rocking platform for 1 hr at room temperature. The solution was then changed to 250 µl of the same buffer containing 4U of Sau3A1 (NEB), equilibrated to 37° C. in a water bath, and then incubated on a rocking platform in a 37° C. incubator for 45 min. The plug was transferred to a 1.5 ml microcentrifuge tube and incubated at 68° C. for 30 mm to inactivate the protein, e.g., enzyme, and to melt the agarose. The agarose was digested and the DNA dephosphorylased using Gelase and HK-phosphatase (Epicentre), respectively, according to the manufacturer's recommendations. Protein was removed by gentle phenol/chloroform extraction and the DNA was ethanol precipitated, pelleted, and then washed with 70% ethanol. This partially digested DNA was resuspended in sterile H$_2$O to a concentration of 2.5 ng/µl for ligation to the pFOS1 vector.

PCR amplification results from several of the agarose plugs (data not shown) indicated the presence of significant amounts of archacal DNA. Quantitative hybridization experiments using rRNA extracted from one sample, collected at 200 m of depth off the Oregon Coast, indicated that planktonic archaeal in (this assemblage comprised approximately 4.7% of the total picoplankton biomass (this sample corresponds to "PACl"-200 m in Table 1 of DeLong et al., High abundance of Archaeal in Antarctic marine picoplankton, Nature, 371:695–698, 1994)). Results from archaeal-biased rDNA PCR amplification performed on agarose plug lysates confirmed the presence of relatively large amounts of archaeal DNA in this sample. Agarose plugs prepared from this picoplankton sample were chosen for subsequent fosmid library preparation. Each 1 ml agarose plug from this site contained approximately $7.5\times10^5$ cells, therefore approximately $5.4\times10^4$ cells were present in the 72 µl slice used in the preparation of the partially digested DNA.

Vector arms are prepared from pFOS1 as described (Kim et al., Stable propagation of cosmid sized human DNA inserts in an f-factor based vector, *Nucl. Acids Res.*, 20:10832–10835, 1992). Briefly, the plasmid is completely digested with AstII, dephosphorylated with HK phosphatase, and then digested with BamHI to generate two arms, each of which contains a cos site in the proper orientation for cloning and packaging ligated DNA between 35–45 kbp. The partially digested picoplankton DNA is ligated overnight to the pFOS1 arms in a 15 µl ligation reaction containing 25 ng each of vector and insert and 1U of T4 DNA ligase (Boehringer Mannheim). The ligated DNA in four microliters of this reaction is in vitro packaged using the Gigapack XL packaging system (Stratagene), the fosmid particles transfected to *E. coli* strain DH10B (BRL), and the cells spread onto $LB_{cm15}$ plates. The resultant fosmid clones are picked into 96-well microliter dishes containing $LB_{cm15}$ supplemented with 7% glycerol. Recombinant fosmids, each containing ca. 40 kb of picoplankton DNA insert, have yielded a library of 3.552 fosmid clones, containing approximately $1.4 \times 10^8$ base pairs of cloned DNA. All of the clones examined contained inserts ranging from 38 to 42 kbp. This library is stored frozen at −80° C. for later analysis.

Example 4

Normalization of DNA from Environmental Samples

Prior to library generation, purified DNA from an environmental sample can be normalized. DNA is first fractionated according to the following protocol:

Sample composed of genomic DNA is purified on a cesium-chloride gradient. The cesium chloride (Rf=1.3980) solution is filtered through a 0.2 µm filter and 15 ml is loaded into a 35 ml OptiSeal tube (Beckman). The DNA is added and thoroughly mixed. Ten micrograms of bis-benzimide (Sigma; Hoechst 33258) is added and mixed thoroughly. The tube is then filled with the filtered cesium-chloride solution and spun in a VTi50 rotor in a Beckman L8-70 Ultracentrifuge at 33.000 rpm for 72 hours. Following centrifugation, a syringe pump and fractionator (Brandel Model 186) are used to drive the gradient through an ISCO UA-5 UV absorbance detector set to 280 nm. Peaks representing the DNA from the organisms present in an environmental sample are obtained.

Normalization is then accomplished as follows:
I. Double-stranded DNA sample is resuspended in hybridization buffer (0.12 M $NaH_2PO_4$, pH 6.8/0.82 M NaCl/1 mM EDTA/0.1% SDS).
II. Sample is overlaid with mineral oil and denatured by boiling for 10 minutes.
III. Sample is incubated at 68° C. for 12–36 hours.
IV. Double-stranded DNA is separated from single-stranded DNA according to standard protocols (Sambrook, 1989) on hydroxyapatite at 60° C.
V. The single-stranded DNA fraction is desalted and amplified by PCR.

The process is repeated for several more rounds (up to 5 or more).

Example 5

Figure 6:
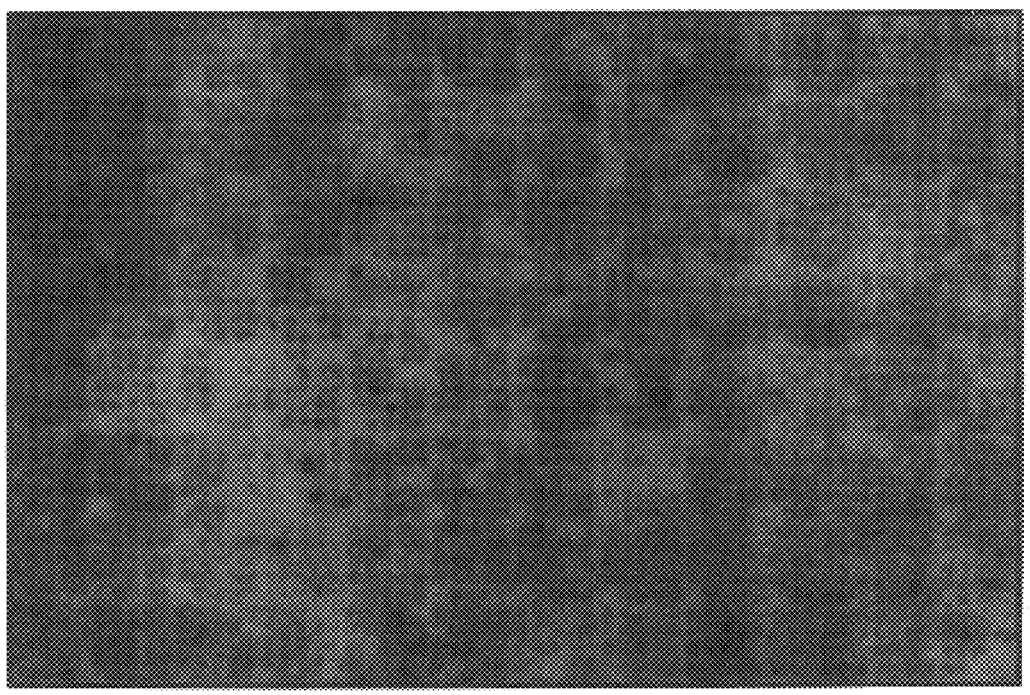
FIG. 6 shows a high density filter array of environmental fosmid clones probed with a labeled oligonucleotide probe. The 2400 arrayed clones contain approximately 96 million base pairs of DNA cloned from a naturally occurring microbial community.

Hybridization Screening of Libraries Generated in Prokaryotes and Expression Screening in Metabolically Rich Hosts Hybridization screening may be performed on fosmid clones from a library generated according to the protocol described in Example 3 above in any fosmid vector. For instance, the pMF3 vector is a fosmid based vector which can be used for efficient yet stable cloning in *E. coli* and which can be integrated and maintained stably in *Streptomyces coelicolor* or *Streptomyces lividans*. A pMF3 library generated according to the above protocol is first transformed into *E. coli* DH10B cells. Chloramphenicol resistant transformants containing tom or oxy are identified by screening the library by colony hybridization using sequences designed from previously published sequences of oxy and tom genes. Colony hybridization screening is analyzed by restriction digestion and PCR to confirm that they contain the complete biosynthetic pathway. (See FIG. 6).

Alternatively, DNA from the abovementioned fosmid clones may be used in a amplification reaction designed to identify clones positive for an entire pathway. For example, the following sequences may be employed in an amplification reaction to amplify a pathway encoding the antibiotic gramicidin (gramicidin operon), which resides on a 34 kbp DNA fragment potentially encoded on one fosmid clone:

Primers

5'CACACGGATCCGAGCTCATCGATAGGCATGTGTTTAACTTCTTGTCATC 3' (SEQ ID NO:2)

5'CTTATTGGATCCGAGCTCAATTGCTGAAGAGTTGAAGGAGAGCATCTTCC 3' (SEQ ID NO:3)

Amplification reaction

| | |
|---|---|
| 1 µl | fosmid/insert DNA |
| 5 µl | each primer (50 ng/µl) |
| 1 µl | Boehringer Mannheim EXPAND Polymerase from their EXPAND kit |
| 1 µl | dNTP's |
| 5 µl | 10X Buffer #3 from Boehringer Mannheim EXPAND kit |
| 30 µl | $ddH_2O$ |

PCR Reaction Program
 94° C. 60 seconds
 20 cycles of:
 94° C. 10 seconds
 65° C. 30 seconds
 68° C. 15 minutes
 one cycle of:
 68° C. 7 minutes
 Store at 4° C.

Fosmid DNA from clones that are shown to contain the ocytetracyclin or tetracenomycin polyketide encoding DNA sequences are then used to transform *S. lividans* TK24 Dact protoplasts from Example 6. Transformants are selected by overlaying regeneration plates with hygromycin (pMF5). Resistant transformants are screened for bioactivity by overlaying transformation plates with 2 ml of nutrient soft agar containing cells of the test organisms *Escherichia coli* or *Bacillus subtilis*. *E. coli* is resistant to the thiostrepton concentration (50 mg/ml) to be used in the overlays of pMF3 clones but is sensitive to oxytetracyclin at a concentration of 5 mg/ml. The *B. subtilis* test strain is rendered resistant to thiostrepton prior to screening by transforming with a thiostrepton marker carried on pHT315. Bioactivity is demonstrated by inhibition of growth of the particular test strain around the *S. lividans* colonies. To confirm bioactivity, presumptive active clones are isolated and cultures extracted using a moderately polar solvent, methanol. Extractions are prepared by addition of methanol in a 1:1 ratio with the clone fermentation broth followed by overnight shaking at 4° C. Cell debris and media solids in the aqueous phase are then separated by centrifugation. Recombinantly expressed compounds are recovered in the solvent phase and may be concentrated or diluted as necessary. Extracts of the clones are aliquoted onto 0.25-inch filter disks, the solvent allowed to evaporate, and then placed on the surface of an overlay containing the assay organisms. Following incubation at appropriate temperatures, the diameter of the clearing zones is measured and recorded. Diode array HPLC, using authentic oxytetracyclin and tetracenomycin as standards, can be used to confirm expression of these antibiotics from the recombinant clones.

Rescue of Chromosmally Integrated Pathways

Sequence analysis of chromosomally integrated pathways identified by screening can be performed for confirmation of the bioactive molecule. One approach which can be taken to rescue fosmid DNA from *S. lividans* clones exhibiting bioactivity against the test organisms is based on the observation that plasmid vectors containing IS117, such as pME3, are present as circular intermediates at a frequency of 1 per 10–30 chromosomes. The presumptive positive clones can be grown in 25 ml broth cultures and plasmid DNA isolated by standard alkaline lysis procedures. Plasmid DNA preps are then used to transform *E. coli* and transformants are selected for $Cm^r$ by plating onto LB containing chloramphenicol (15 mg/ml). Fosmid DNA from the *E. coil* $Cm^r$ transformants is isolated and analyzed by restriction digestion analysis, PCR, and DNA sequencing.

Example 6

Screening Libraries of Genes for Compounds Affecting the Interaction of other Molecules in Prokaryotes Large insert libraries generated according to Examples 2 and 3 can be screened for compounds which affect the interaction of other molecules using the following method (s):

Genes encoding two interacting proteins are fused to a wild type and a mutant LexA DNA binding domain (the mutant is a truncated LexA protein devoid of its own oligomerization domain and is termed LexA408). LexA is an efficient transcriptional repressor in *E.coli* only if it acts as a dimer. This property is used to exchange the LexA dimerization domain by heterologous interacting motifs to recover repression. The non-covalent interaction between the hybrid proteins is probed by their capacity to restore the repressor activity of truncated LexA proteins (LexA408).

The interaction or association of the fused proteins is specifically measured using a reporter gene controlled by a hybrid sulA operator containing a wild type half-site and a mutated half-site (op408/op+) in a reporter strain (SU202). The lacZ reporter gene is under control of the op408/op+ hybrid operator using the sulA promoter, the most tightly repressed naturally occurring SOS promoter.

SU202 cells containing the interacting proteins from above are co-transformed with a library of genes expressing small molecules, such as those generated in the Examples above. Cells are then screened for GFP expression; an indication of inhibition of the protein-protein interaction.

Example 7

Screening Libraries of Genes for Compounds Affecting the Interaction of other Molecules in Eukaryotes Commercially available two-hybrid systems can be purchased from Clontech Laboratories (Palo Alto, Calif.) or Stratagene Cloning Systems (La Jolla, Calif.). Genes encoding interacting molecules are cloned into vectors provided, and cotransformed into appropriate yeast strains provided. Interaction can be confirmed utilizing methods provided. Cells containing the interacting proteins are then transformed utilizing methods well known in the art with a library of genes expressing small molecules, such as those generated in the Examples above. Cells are then assayed for an increase or decrease of the expression levels of the detectable molecule ($\beta$-galactosidase) an indication of an effect on the protein-protein interaction.

I. Literature Cited

Adams, M. W. W., Kelly, R. M., *Chemical and Engineering News*, 1995, Dec. 18.

Amann, R., Ludwig, W., and Schleifer, K. -H. *Microbiological Reviews*, 1995, 59, 143.

Barnes, S. M., Fundyga, R. E., Jeffries, M. W. and Pace, N. R. *Proc. Nat. Acad. Sci. USA*, 1994, 91, 1609.

Bateson M. M., Wiegel, J., Ward, D. M., *System. Appl. Microbiol*. 1989, 12, 1–7

Betz, J. W., Aretz, W., Hartel, W., *Cytometry*, 1984, 5, 145–150

Davey, H. M., Kell, D. B., *Microbiological Reviews*, 1996, 60, 4, 641–696

Diaper, J. P., Edwards, C., *J. Appl. Bacteriol.*, 1994, 77, 221–228

Enzyme Nomenclature, *Academic Press*: NY, 1992.

Faber, Biotransformation in organic chemistry 2 nd edition, *Springer Verlag*, 1995.

Fiering, S. N., Roeder, M., Nolan, G. P., Micklem, D. R., Parcks, D. R., Herzenberg, L. A. *Cytometry*, 1991, 12, 291–301.

Giovannoni, S. J., Britschgi, T. B., Mover, C. L., Field, K. G., *Nature*, 1990 345, 60–63

Murray, M. G., and Thompson, W. F., *Nucl. Acids Res.*, 1980, 8, 4321–4325

Nolan, G. P., Fiering, S., Nicolas, J., F., Herzenberg, L. A., *Proc. Natl. Acad. Sci. USA*, 1988, 85 2603–2607.

Plovins A., Alvarez A. M., Ibanez M., Molina M., Nombela C., Appl. Environ. Microbiol., 1994, 60, 4638–4641.

Short, J. M., Fernandez, J. F. Sorge, J. A., and Huse, W. *Nucleic Acids Res*., 1988, 16, 7583–7600.

Short, J. M., and Sorge, J. A. *Methods in Enzymology*, 1992, 216, 495–508.

Tonkovich, A., L., Gerber, M. A., US Department of Energy, Office of Industrial Technology, Biological and Chemical Technologies Research Program under contract DE-AC06-76RLO 1830

Torvsik, V. Goksoyr, J. Daae, F. L., *Appl. and Environm. Microbiol*. 1990, 782–787

Wittrup, K. D., Bailey, J. E., Cytometry, 1988, 9, 394–404.

Wrotnowski, *Genetic Engineering News*, 1997, Feb. 1.

What is claimed is:

1. A method for screening for the presence of a molecule that affects the interaction between a first and second molecule, comprising:
   (i) contacting in a cell a first molecule with a second molecule wherein at least one of the first or second molecules is derived from a library made from a mixed population of organisms, wherein association of the first and second molecules in the presence of a third molecule results in the presence of a detectable response by changing expression of a detectable gene or detectable gene product; and
   (ii) comparing the detectable response in the presence of the third molecule and the first and second molecules with the detectable response in the absence of the third molecule, wherein a difference in response is indicative of first and second molecules that interact and a third molecule that affects the interaction between the first and second molecules, thereby identifying the presence of a molecule that affects the interaction of the first and second molecules.

2. The method of claim 1, wherein at least one of the interacting molecules contains a DNA-binding moiety and at least one of the interacting molecules contains a transcriptional activation or a transcriptional repressor moiety.

3. The method of claim 2, wherein the DNA-binding moiety and the transcriptional activation moiety are derived from a single transcriptional activator.

4. The method of claim 2, wherein the DNA-binding moiety and the transcriptional activation moiety are derived from different proteins.

5. The method of claim 1, wherein the detectable signal is produced from a gene encoding a protein selected from the group consisting of β-galactosidase, green fluorescent protein. luciferase, alkaline phosphatase and chloramphenicol acetyl transferase.

6. The method of claim 1, wherein the detectable signal is encoded by a gene present in the host cell.

7. The method of claim 6, wherein the host cell further comprises a first recombinant gene encoding the first molecule, a second recombinant gene encoding the second molecule, or a third recombinant gene encoding the third molecule.

8. The method of claim 7, wherein the host cell contains both the first gene and the second gene and each gene is expressed.

9. The method of claim 7, wherein the host cell contains the first, second and third genes and each gene is expressed.

10. The method of claim 1, wherein the third molecule contains a DNA binding domain and a transcriptional activation domain.

11. The method of claim 1, further comprising, prior to step (i):
   obtaining the mixed population of organisms from an environmental sample; and
   enriching the sample for prokaryotic organisms, thereby creating an enriched environmental sample, wherein said sample is used to generate the library.

12. The method of claim 11, further comprising producing a normalized library, comprising:
   isolating nucleic acids from said enriched environmental sample;
   fractionating the isolated nucleic acids; and amplifying any single-stranded nucleic acids present in the same cell.

13. The method of claim 12, further comprising generating an expression library, comprising:
inserting the amplified and isolated nucleic acids into an expression vector.

14. The method of claim 1, wherein a nucleic acid sequence encoding the third molecule is determined.

15. The method of claim 1, wherein the third molecule is derived from the mixed population of organisms.

* * * * *

SEQUENCE LISTING

<160> NUMBER OF SEQ ID NOS: 3

<210> SEQ ID NO 1
<211> LENGTH: 8
<212> TYPE: DNA
<213> ORGANISM: Artificial Sequence
<220> FEATURE:
<223> OTHER INFORMATION: EcoRI nucleotide linkers

<400> SEQUENCE: 1 ggaattcc                                                                    8

<210> SEQ ID NO 2
<211> LENGTH: 49
<212> TYPE: DNA
<213> ORGANISM: Artificial Sequence
<220> FEATURE:
<223> OTHER INFORMATION: oligonucleotide for PCR

<400> SEQUENCE: 2
cacacggatc cgagctcatc gataggcatg tgtttaactt cttgtcatc                      49

<210> SEQ ID NO 3
<211> LENGTH: 50
<212> TYPE: DNA
<213> ORGANISM: Artificial Sequence
<220> FEATURE:
<223> OTHER INFORMATION: oligonucleotide for PCR

<400> SEQUENCE: 3
cttattggat ccgagctcaa ttgctgaaga gttgaaggag agcatcttcc                     50